US009519753B1

(12) United States Patent
Gerdeman et al.

(10) Patent No.: US 9,519,753 B1
(45) Date of Patent: Dec. 13, 2016

(54) RADIOLOGY WORKFLOW COORDINATION TECHNIQUES

(71) Applicant: Virtual Radiologic Corporation, Minneapolis, MN (US)

(72) Inventors: Kimberlee Gerdeman, Eden Prairie, MN (US); Andrew Grabiel, Eden Prairie, MN (US); Kenneth Leer, Chanhassen, MN (US); Joe Schmugge, Minneapolis, MN (US); Wade J. Steigauf, Bloomington, MN (US); Benjamin Strong, Tucson, AZ (US); Shannon Werb, Minneapolis, MN (US); Angela Yates, Sioux City, IA (US)

(73) Assignee: Virtual Radiologic Corporation, Minneapolis, MN (US)

( * ) Notice: Subject to any disclaimer, the term of this patent is extended or adjusted under 35 U.S.C. 154(b) by 15 days.

(21) Appl. No.: 14/721,637

(22) Filed: May 26, 2015

(51) Int. Cl.
*G06K 9/00* (2006.01)
*G06F 19/00* (2011.01)
*A61B 6/00* (2006.01)
*G06T 7/00* (2006.01)

(52) U.S. Cl.
CPC ........... *G06F 19/321* (2013.01); *A61B 6/5294* (2013.01); *G06T 7/0012* (2013.01); *G06T 2200/24* (2013.01); *G06T 2207/10116* (2013.01); *G06T 2207/30004* (2013.01)

(58) Field of Classification Search
CPC .............. G06F 19/00; A61B 6/00; G06T 7/00
USPC ....................................................... 382/132
See application file for complete search history.

(56) References Cited

U.S. PATENT DOCUMENTS

| 8,214,229 | B2 | 7/2012 | Thorne et al. |
| 8,301,461 | B2 | 10/2012 | Reiner |
| 8,311,847 | B2 | 11/2012 | Kotula et al. |
| 8,612,250 | B2 | 12/2013 | Backhaus et al. |
| 8,612,253 | B2 | 12/2013 | Backhaus et al. |
| 2006/0074711 | A1 | 4/2006 | Mahesh et al. |
| 2007/0005798 | A1 | 1/2007 | Gropper et al. |
| 2007/0038474 | A1 | 2/2007 | Halsted |

(Continued)

OTHER PUBLICATIONS

Ellenbogen, Paul H., et al., "The Radiologist Assistant: What Radiologists Need to Know Now", J Am Coll Radiol, 4, (2007), 461-470.

*Primary Examiner* — Gregory F Cunningham
(74) *Attorney, Agent, or Firm* — Schwegman Lundberg & Woessner, P.A.

(57) ABSTRACT

Systems and methods for coordinating a medical imaging workflow with the use of preparation and coordination actions, and similar pre-processing protocols are disclosed herein. Imaging procedure data from a medical imaging study, such as image data and order data produced from imaging procedures (e.g., radiological imaging procedures) at medical facilities is processed and presented for review to a preparing user. The preparing user is offered the ability to change the display characteristics of image presentation, supplement erroneous or incomplete data and information of the study, open a support request for the study, or associate prior or comparison images with the study. The changes provided by the preparing user within these or other portions of a preparation protocol may be used to affect a subsequent display of the medical imaging study, and in some examples, to affect the assignment of the study in the workflow to particular imaging users.

24 Claims, 12 Drawing Sheets

(56) References Cited

U.S. PATENT DOCUMENTS

| | | |
|---|---|---|
| 2007/0143136 A1 | 6/2007 | Moore |
| 2008/0144897 A1 | 6/2008 | Lal et al. |
| 2008/0292152 A1 | 11/2008 | Nekrich |
| 2009/0172036 A1 | 7/2009 | Marx |
| 2010/0140483 A1* | 6/2010 | Rousso ............. A61K 51/0478 250/362 |
| 2011/0028825 A1* | 2/2011 | Douglas ................ G06F 19/321 600/407 |
| 2011/0257919 A1 | 10/2011 | Reiner |
| 2013/0018674 A1 | 1/2013 | Bedi et al. |
| 2013/0132105 A1 | 5/2013 | Wood-Salomon et al. |
| 2013/0132119 A1 | 5/2013 | Imam et al. |
| 2014/0142969 A1 | 5/2014 | Backhaus et al. |
| 2014/0149942 A1 | 5/2014 | Wood-Salomon |

\* cited by examiner

FIG. 5A

| Worklist | Signed | Search | OC Support | Auto QA | RAD Portal | STATdx | Admin |

Volume Overview
Emergent Arrived         44
Emergent > 30 Min         0
Radiologist Online       44
Radiologist On Break      0

Avg Emergent Countdown
029
Ratio = 1.00

[Read]

| Patient | Modal | Type | Status | Procedure(s) | Images | Facility | ST | MRN | Count |
|---|---|---|---|---|---|---|---|---|---|
| Test001, CR | XR | P | Ready | • XR CHEST, Arrived | 10 | VRC Training Hospital - 1 | US | vRadCRO | 20 |
| Test002, CR | XR | P | Ready | • XR CHEST SINGLE VIEW PORTABLE, Arrived | 10 | VRC Training Hospital - 1 | US | vRadCRO | 20 |
| Test003, CR | XR | P | Ready | • XR CHEST, Arrived | 10 | VRC Training Hospital - 1 | US | vRadCRO | 20 |
| Test004, CR | XR | P | Ready | • XR WRIST, Arrived | 10 | VRC Training Hospital - 1 | US | vRadCRO | 20 |
| Test005, CR | CT | P | Ready | • CT ABDOMEN & PELVIS, Arrived | 10 | VRC Training Hospital - 1 | US | vRadCRO | 20 |
| Test006, CR | XR | P | Ready | • XR FINGER, Arrived | 10 | VRC Training Hospital - 1 | US | vRadCRO | 20 |
| Test001, US | US | P | Ready | • US ABDOMEN, Arrived | 10 | VRC Training Hospital - 1 | US | vRadCRO | 20 |
| Test002, US | US | P | Ready | • US PREG LESS THAN 14 WKS, Arrived | 10 | VRC Training Hospital - 1 | US | vRadCRO | 20 |
| Test003, US | US | P | Ready | • US SCROTAL/TESTICULAR, Arrived | 10 | VRC Training Hospital - 1 | US | vRadCRO | 20 |

RADIOLOGY WORKFLOW COORDINATION TECHNIQUES

TECHNICAL FIELD

Embodiments pertain to techniques and systems for processing electronic imaging data obtained from medical imaging procedures. Some embodiments relate to data processing mechanisms in medical imaging workflows involving the use of coordinators, assistants, and other human or automated actors.

BRIEF DESCRIPTION OF THE DRAWINGS

FIG. 5A illustrates a worklist graphical user interface for management of medical imaging studies by a preparing user according to an example described herein.

FIG. 6A illustrates a worklist graphical user interface for management of medical imaging studies by an evaluating user according to an example described herein.

FIG. 6B illustrates a study reporting graphical user interface for management of a medical imaging study by an evaluating user according to an example described herein.

DETAILED DESCRIPTION

Figure 1:
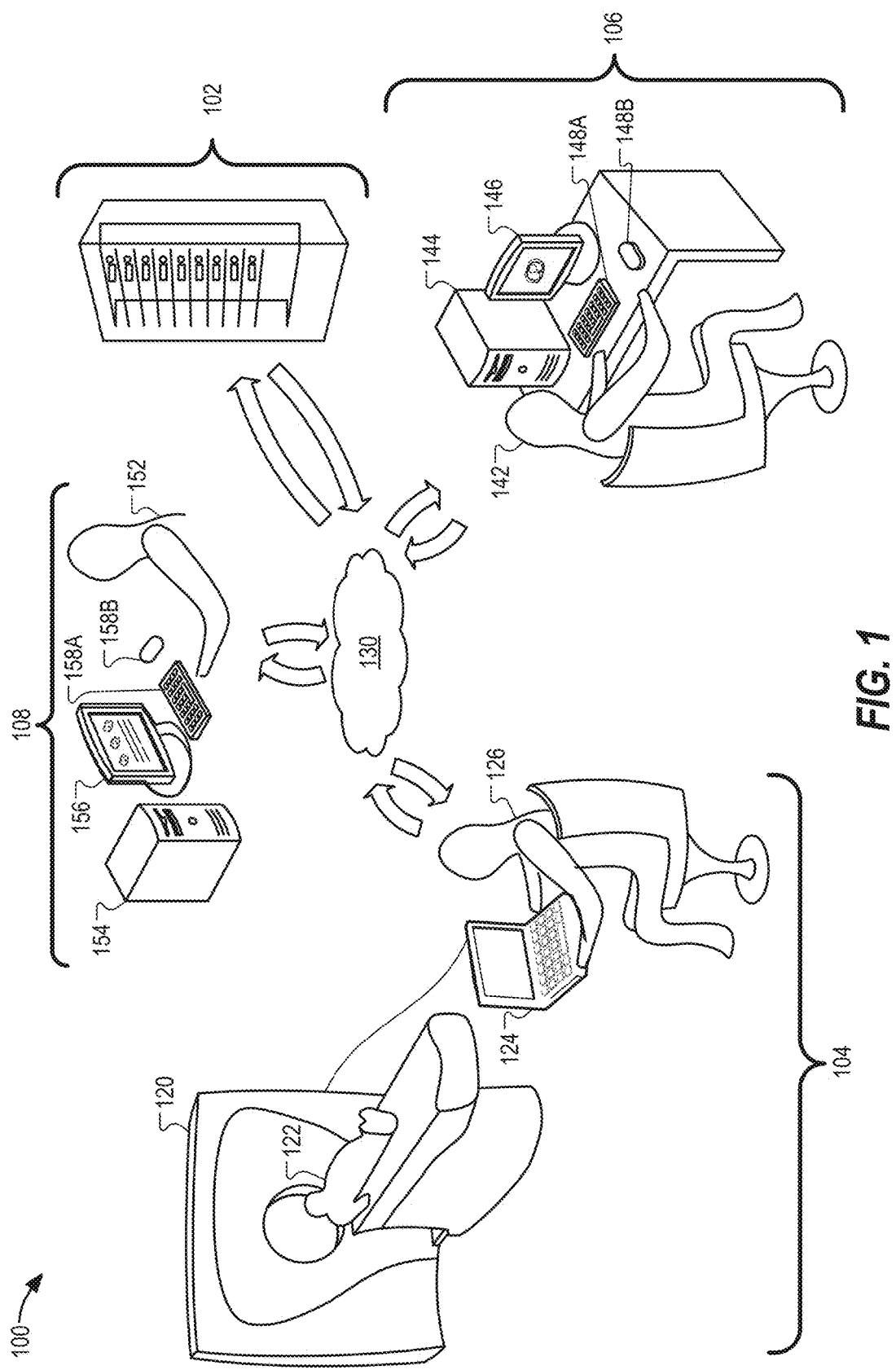
FIG. 1 illustrates a system configuration enabled for processing, coordinating, preparing, and assigning medical imaging data and medical imaging requests according to an example described herein.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments.

The present disclosure illustrates various techniques and configurations that enable pre-processing and coordination activities in a medical imaging data environment. For example, these pre-processing and coordination activities may be performed upon medical imaging procedure data produced as part of a medical imaging study. The medical imaging procedure data may include image data captured by an imaging modality, and order data (such as data indicating a request for a radiological image read), each produced to facilitate a medical imaging evaluation (such as a radiology read to be performed by a radiologist or a diagnostic evaluation by another qualified medical professional). The pre-processing and coordination activities may include active preparation steps that are accompanied by actions performed on the medical imaging procedure data prior to, or concurrent with, the medical imaging evaluation.

The pre-processing and coordination activities enabled by the present techniques may include activities such as: correcting errors or supplying incomplete information for data fields in the medical imaging procedure data; adjusting window/level, increasing or reducing image sharpness, changing imaging hanging arrangements, and affecting other visual characteristics of image displays for images in the medical imaging procedure data; compiling prior images and reports, identifying or labeling anatomical features, implementing measurements, or identifying the most relevant images in an imaging study; providing initial reports and diagnostic information for the imaging study; and performing other relevant analysis and modifications for the medical imaging procedure data.

As further discussed herein, the results of these pre-processing and coordination activities may be used to drive assignments and evaluation activities for the medical imaging procedure data. For example, information that is provided or supplemented in the pre-processing activity may assist the assignment of a request for evaluation of the image to an evaluator such as a remote radiologist. The pre-processing and coordination activities may also provide meta-data elements that are added for downstream use by evaluators, reviewers, and medical professionals. Further, the pre-processing and coordination activities may be used to establish, modify, and bookmark different states of the medical imaging evaluation process, including customized image viewing states that can be resumed at remote workstations or locations. The pre-processing and coordination activities thus may be used to provide improved quality and accuracy of the data used in the medical imaging evaluation process, in addition to improved efficiency (and workflow routing) of the data and the associated reading or diagnostic procedures occurring in the medical imaging evaluation process.

In some of the following examples, reference is made to radiology medical imaging procedures (e.g., computed tomography (CT), magnetic resonance imaging (MRI), Ultrasound, and X-ray procedures, etc.) and diagnostic evaluation of the images produced from such imaging procedures that would be performed with an image evaluation (e.g., radiology read) by a licensed and credentialed radiologist. It will be understood that the applicability of the presently described techniques and systems will extend to a variety of medical procedures and specialties, including those not involving traditional radiology imaging modalities. Such specialties include, but are not limited to, pathology, medical photography, medical data measurements such as electroencephalography (EEG) and electrocardiography (EKG) procedures, cardiology data, neuroscience data, preclinical imaging, and other data collection procedures occurring in connection with telemedicine, telepathology, remote diagnostics, and other applications of medical procedures and medical science. Accordingly, the performance of the data coordination, pre-processing, and workflow preparation techniques described herein may apply to a variety of medical data types and settings.

FIG. 1 provides an illustration of an example medical imaging system configuration 100 (e.g., a radiology imaging configuration), which enables the processing of data from medical imaging procedures according to an example described herein. The system configuration 100 may be used for capturing medical image data in one location and for reviewing medical images associated with the data in another location. The system configuration 100 may include many geographically separated imaging devices and many image review terminals. The system configuration 100, in a radiology setting, may be embodied as a remote teleradiology system connected to a plurality of healthcare locations, as a localized radiology system used in a single hospital, healthcare provider network, or private radiology practice. The system configuration 100 may also operate as an information processing network used to process data from respective imaging procedures regardless of the location of an eventual imaging evaluation.

For purposes of illustration, the system configuration 100 depicted in FIG. 1 includes an imaging system 104, an imaging order processing system 102, an image review system 106, and a data pre-processing and coordination system 108. The imaging system 104, for example, may include an imaging device 120, such as a CT scanner, a MRI scanner, or another imaging system (e.g., a radiology imaging modality). Using an energy source such as x-rays or magnetic fields, for example, the imaging device 120 may capture image data associated with a subject 122 (e.g., a patient).

The imaging device 120 may be controlled by a technician 126 at the medical facility through the use of a workstation terminal or other electronic input control 124. Prior to the technician 126 conducting the imaging procedure for a patient, information may be entered into the electronic input control 124. Information from an electronic medical record (EMR) or healthcare information system (HIS) may also be accessed or updated for the imaging procedure. Relevant information and metadata for the imaging procedure may be placed within the image data itself, or within another data store for further access and processing. For example, the imaging device 120 may produce radiological images generally consistent with the Digital Imaging and Communications in Medicine (DICOM) format, other industry-accepted standards, or proprietary standards.

Consistent with the appropriate image format, the images produced by the image data source may include metadata. This metadata may be generated by the imaging device 120, from input collected by the electronic input control 124, or from input from a HIS. Further, a series of images produced by the image data source may be obtained directly by the imaging device 120 in the facility shown in FIG. 1, or may be transferred in whole or in part from another image capturing device or image data store connected to the imaging device 120 or the medical facility's local network. The imaging data source may also include data transmitted through use of a local facility imaging server (not shown), such as a DICOM server or other Picture Archiving and Communication System (PACS). The metadata within each imaging data file may include identification information such as a patient identifier and an identifier of the series of images, in addition to information about the type of imaging modality and the techniques used to obtain the images. Further, for images formatted according to the DICOM standard, data fields such as a unique image identifier, a unique study identifier, the patient's name, and the facility from which the image originates may be included.

The image data generated by the imaging device 120 may include a series of two-dimensional images, with the collection of some identifiable series of images typically referred to as a "study". In some implementations, the image data may be used to produce a three-dimensional model that can be further manipulated and reformatted for generating two-dimensional (or three-dimensional) images. In other implementations, the image data may include three-dimensional models or graphical data generated by the imaging device 120 or intermediate processing systems. Image data captured by the imaging device 120 may be stored and processed by the imaging order processing system 102 or another local or remote imaging device server (e.g., one or more computers with a processor and a memory), and may be provided to other systems and computers in the system configuration 100 through network 130 (e.g., an intranet or the Internet).

In some implementations, medical imaging procedure data provided to the imaging order processing system 102 results in data being stored and processed by one or more computers. For example, the imaging order processing system 102 may determine that the medical imaging procedure data is to be forwarded to a viewing system evaluating user 142 (e.g., a radiologist) at an image review system 106. As shown, image data may be provided by the imaging order processing system 102 through the network 130 to the image review system 106. Additionally, the medical imaging procedure data provided to the imaging order processing system 102 results in the image data or the order data (or both) being processed by the data pre-processing and coordination system 108. As further detailed herein, this data may be handled by the data pre-processing and coordination system 108 prior to, in parallel with, or at the same time as the provision or assignment of the image data to the image review system 106.

The image review system 106, for example, may include an image display server 144 (e.g., one or more computers with a processor and a memory), a display device 146 (e.g., a monitor), and input devices 148A-148B (e.g., keyboards, computer mice, joysticks, touch interfaces, voice recognition interfaces, and the like). In some implementations, image data may be processed by the image display server 144 and visually presented to the evaluating user 142 as one or more images at the display device 146. Using the input devices 148A-148B, the evaluating user 142 may interact with the presented images, for example, by manipulating one or more user controls included in a graphical user interface presented at the display device 146 in association with the images. For example, the evaluating user 142 may view an image (or a series of related images), and may specify one or more image adjustments, such as zooming, panning, rotating, changing contrast, changing color, changing view angle, changing view depth, changing rendering or reconstruction technique, and the like. By viewing and interacting with presented image data and with the user interface, for example, the evaluating user 142 may indicate a diagnostic finding or produce a diagnostic finding output related to a radiological imaging procedure performed on the subject 122.

The image pre-processing and coordination system 108, for example, may also include a data processing server 154 (e.g., one or more computers with a processor and a memory), a display device 156 (e.g., a monitor), and input devices 158A-158B (e.g., keyboards, computer mice, joysticks, touch interfaces, voice recognition interfaces, and the like). In some implementations, medical imaging procedure data may be processed by the data processing server 154 and visually presented to a preparing user 152 within a graphical user interface at the display device 156. In some implementations, the graphical user interface may be interacted with by the preparing user 152 to effect processing and changes to the medical imaging procedure data with the data processing server 154. In some implementations, the data processing server 154 may perform automated processing and changes to the medical imaging procedure data; in other examples, the data processing server 154 creates additional data used to record and track changes from the medical imaging procedure data.

When the imaging order processing system 102 receives the image, it may process the image with an image server. This processing may include compressing or converting the image to a different format using a compressor/converter module. This image server may also operate to extract metadata from each image file in a series of images. For example, the extracted metadata may include header data for the image providing patient information and hospital information for the hospital that sent the image. The image server may then store all or part of the extracted information in a study record that may be correlated with appropriate orders and studies. The imaging order processing system 102 may operate to process related orders or correlate a particular order (and order data) with a particular set of study images (and image data). In some examples, the imaging order processing system 102 operates to perform a lateral and horizontal movement of studies between an onsite facility and a remote/cloud location with a closely orchestrated feed utilizing HL7 (Health Level 7) and DICOM standards.

Figure 2:
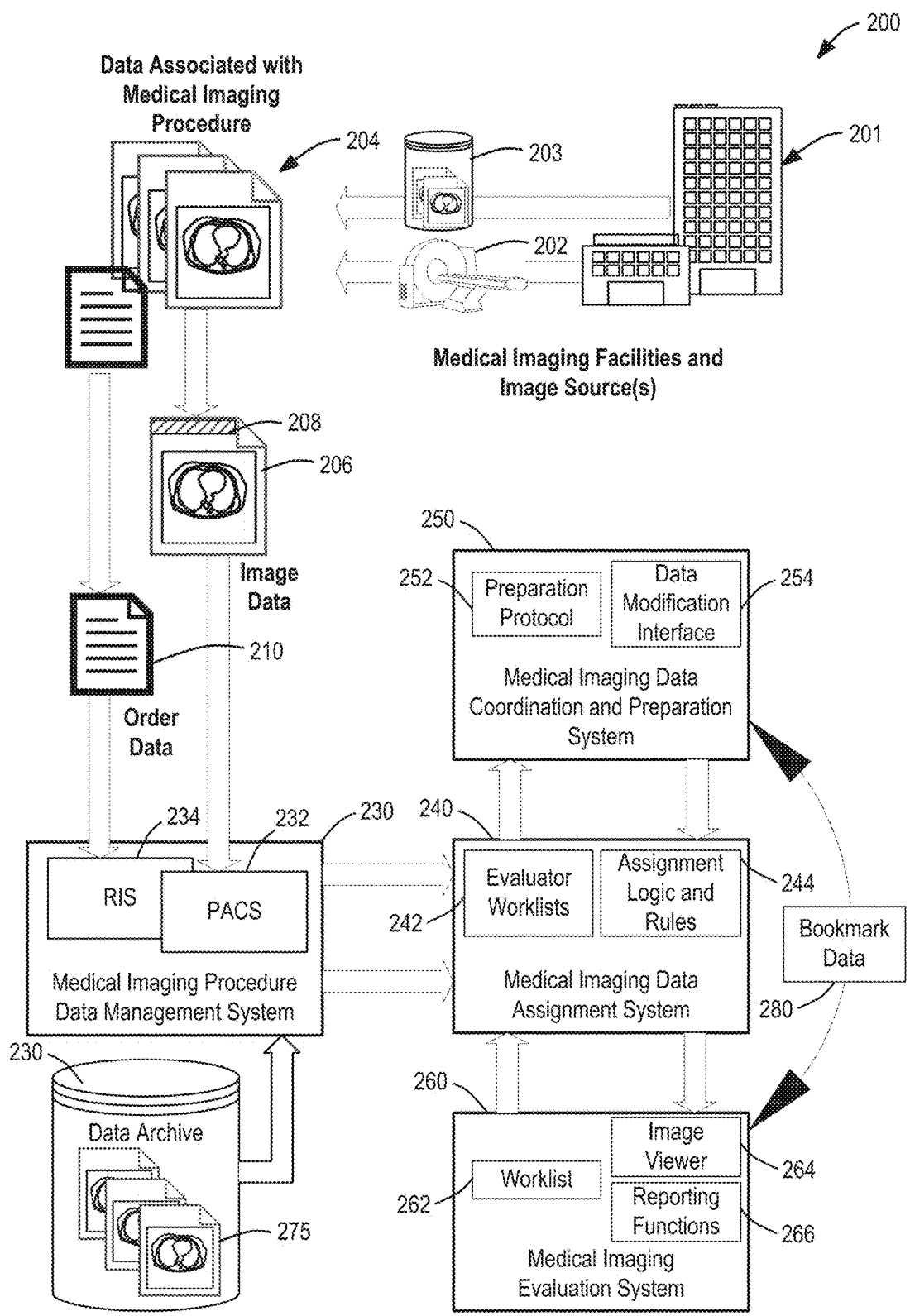
FIG. 2 illustrates system operations in a workflow for coordination and preparation of medical imaging data produced from a medical imaging procedure according to an example described herein.

FIG. 2 illustrates a system operations diagram 200 of an example workflow for generating and routing a set of data produced from a particular medical imaging study (e.g., a radiology study) with use of coordination and pre-processing activities according to an example described herein. The system operations diagram 200 is depicted as including image data 206 and order data 210 originating from data of a medical imaging procedure (produced from an imaging modality 202 or a data store 203 (or both) at one or more medical imaging facilities 201), with the combination of image data and order data collectively referred to as imaging procedure data 204. It will be understood, however, that the imaging procedure data 204 may also be accompanied, integrated, or associated with information from medical information systems (e.g., EMR data, HIS data, and the like) that is not necessarily produced from the medical imaging procedure.

The system operations diagram 200 illustrates a series of operations executable with an image processing system, such as the system configuration 100 or specific components of the imaging order processing system 102 and data pre-processing and coordination system 108. These operations include the receipt and processing of the imaging procedure data 204 (e.g., radiology study data, including one or both of a radiology order and a radiology imaging data) originating from a particular medical imaging facility or imaging source of the medical imaging facilities 201. This imaging procedure data 204 is processed to obtain identifying data associated with the medical imaging procedure, including an identification of imaging characteristics, type of the imaging procedure, and associated information related to the evaluation of the imaging data. For example, the medical imaging procedure data may include image data 206 and image metadata 208, where the image metadata 208 may include identification information such as a patient identifier and an identifier of the series of images, in addition to information about the type of imaging modality and the techniques used to obtain the images. The imaging procedure data 204 also may include order data 210 for an associated order to perform the diagnostic evaluation of the image data. For example, the order data 210 may be associated with data from an HL7 Order Message (ORM) sent when a healthcare provider requests a service, procedure, or treatment for a patient.

The imaging procedure data 204 may be provided to or assigned within the medical imaging procedure management system 230 for further use and processing of the image data 206 and the order data 210. For example, the medical image procedure management system 230 may include a PACS module 232, where the PACS module 232 provides image storage and access features for the image data 206. The medical imaging procedure management system 230 may further include a Radiology Information System (RIS) module 234, where the RIS module 234 provides information processing functions for the order data 210. The PACS module 232 and RIS module 234 may organize, correlate, and process the image data 206, image metadata 208, and order data 210.

Data from the medical image procedure management system 230 may be provided to a data assignment system 240 for purposes of assignment to one or more selected evaluators for diagnostic interpretation, analysis, or other evaluation of the image data 206. For example, the data assignment system 240 may maintain a series of evaluator worklists 242 which are used to propagate the assignment of studies to respective evaluators. The data assignment system 240 may use a set of assignment logic and rules 244 to determine the appropriate assignment of studies to the respective evaluators. Accordingly, the data assignment system 240 can operate to provide imaging data to an evaluation system 260 operated by a respective evaluator. The evaluation system 260 may include a worklist 262 of assigned studies to review by a particular evaluating user; an image viewer 264 to output and control the display of various images from the image data; and reporting functions 266 to collect and compile a diagnostic report for medical findings from the image data.

Data from the medical image procedure management system 230 also may be provided to a data coordination and preparation system 250 that is used to review, prepare, correct, modify, augment, or change the imaging procedure data 204 in connection with the assignment and evaluation functions described above. For example, the data coordination and preparation system 250 may apply a preparation protocol 252 to perform automated or computer-assisted operations to modify the imaging procedure data 204 (or to modify a working copy of the imaging procedure data 204).

The data coordination and preparation system 250 may also include a data modification interface 254, which may be embodied by a graphical user interface, to allow a preparing user to make changes to the imaging procedure data 204. For example, if a preparing user determines that prior comparison study data (e.g., historical imaging procedure data 275) is not properly included in (or linked or associated) to the imaging procedure data 204, the preparing user may access a particular set of imaging procedure data 275 from a data archive 270 (or, from the data store 203 at a site of the medical imaging facility 201), and associate the particular set of imaging procedure data 275 to the imaging procedure data 204. In a similar example, the preparing user may perform operations to correct known errors, update visual characteristics, for either order data 210 or image data 206.

As a result of these changes or additions to the imaging procedure data 204, the data assignment system 240 may provide a more accurate assignment. For example, if a particular specialty is identified as a result of the correction, or information that affects the assignment of the study to a particular evaluator is corrected or augmented, the assignment will be more accurate and less susceptible to encounter technical delays, re-transmission, or re-assignment.

The updates that are provided or added to the imaging procedure data 204 may be changes to representations of display states for the imaging procedure data 204. For example, changes to the data may be provided within a set of image display states indicated by preparation data such as bookmark data 280. The bookmark data 280 may be established or updated by the data coordination and preparation system 250 to track a state for a display of the image data 206 that can be subsequently accessed by the evaluation system 260. The bookmark data 280 may be used to establish relevant views and image display states that assist the display of the study, series, or individual images to the evaluating user.

In some examples, the bookmark data 280 is communicated as part of an "image manifest" that is used to specify the image display characteristics (e.g., image presentation and organization characteristics) of a particular image study state for a plurality of images. The state for the display of the image data 206 may be updated to include various changes to presentation features, image orientations, image positions, and other changes from a default or unmodified display state of the image data. Accordingly, the preparing user may utilize the data modification interface 254 to create and update display changes perfected in the bookmark data 280. Changes may be received from a preparing user with the use of an image viewer in the data modification interface 254, as the preparing user previews or demonstrates the image display that will occur at the evaluation system 260. Other types of preparation data may be established or otherwise updated by the preparing user.

Although not expressly depicted within FIG. 2, other fields of information may be established or updated by the data coordination and preparation system 250 for provision to and use by the evaluation system 260. These fields of information may include measurements, image annotations, preliminary image findings and report data, order data modifications, and the like, and data values for these fields of information may be received within the data modification interface 254. These fields of information may be communicated via the bookmark data 280, such as bookmark data included with the image manifest that is read by the data coordination and preparation system 250. The fields of information may also be used to provide updates to the PACS 232 or RIS 234 modules, or other components of the medical image procedure management system 230. In other examples, the fields of information may be communicated as state data to the data assignment system 240, or propagated throughout the system in diagram 200 to evaluating users as part of display preferences, assignment data, or other relevant data values.

In some examples, the image display state that is established by the data coordination and preparation system 250 (e.g., specified in the bookmark data 280) differs from that established by hanging protocols. Whereas a hanging protocol may be used at the evaluation system 260 to arrange multiple series of images in a display relative to each other, a hanging protocol is typically not knowledgeable about orientation of the images within the series. Further, a hanging protocol typically only evaluates metadata, whereas the data coordination and preparation system 250 may be used to evaluate the actual display that will occur for rendering and evaluation of the image data. The use of human preparing users and advanced processing algorithms at the data coordination and preparation system 250 thus provides for more flexibility and accuracy for visual presentation changes than is available with traditional techniques and rules for organizing medical image displays.

The image display state that is established by the data coordination and preparation system 250 thus allows the full reorientation, position, and modification of a display state, to customize a display state of one or more images by actions of a preparing user. The image display state that is established by the data coordination and preparation system 250 accomplishes these modifications through the use of the image manifest that is communicated to respective systems. The image manifest may be used to provide a uniform way to evaluate and organize images, despite the original format of the study and discrepancies in format or organization from the original modality or medical imaging facility. Accordingly, the involvement of a preparing user and the use of a preparation protocol at the data coordination and preparation system 250 will result in time, processing, and technical efficiencies, to enable an evaluating user (e.g., a radiologist) to more quickly access data of improved quality, in a standardized and uniform format.

Figure 3:
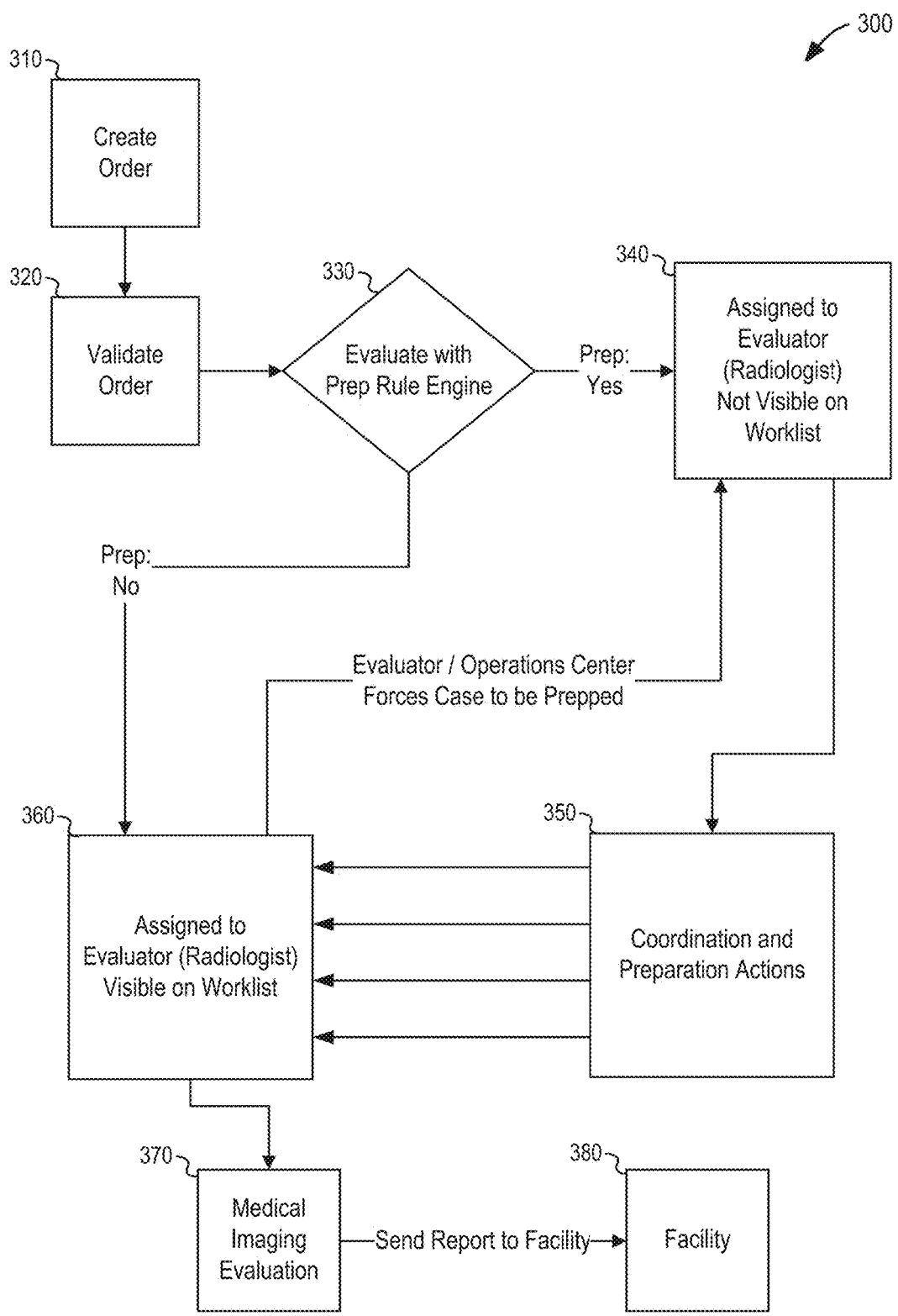
FIG. 3 illustrates a flowchart of a process for preparation and assignment of a medical imaging order according to an example described herein.

FIG. 3 illustrates a flowchart 300 of a preparation and assignment process that may be performed in an image data processing system, such as the systems depicted in FIGS. 1 and 2, according to an example described herein. This preparation and assignment process may be initiated through the receipt of a request for a medical imaging evaluation from a medical facility, for example, at a radiology practice or at a teleradiology provider. In other examples, portions of this preparation and assignment process may be initiated as a standalone data verification process, such as may be performed by a third party vendor to validate or evaluate imaging procedure data.

In the flowchart 300, various operations are performed to validate the medical imaging evaluation request, which as depicted, may take the form of an order (e.g., image read request) to evaluate an imaging study. The workflow operations are commenced with the creation of the imaging evaluation order (operation 310), or a similar access or retrieval of the imaging evaluation order. The operations continue with the validation of the imaging evaluation order (operation 320). This validation may involve computer-assisted or computer-exclusive analysis of data, to ensure that data fields necessary to perform the imaging evaluation are provided or accessible. If necessary fields are not present in the order data or in image data associated with the order, then the study may be immediately escalated to a service center (such as an operations center), rejected, or flagged.

The operations of the flowchart 300 continue with the evaluation of the medical imaging procedure data using a prep rule engine (evaluation 330). The prep rule engine may evaluate various rules and conditions to determine whether further preparation and coordination of the study is allowed or preferable. For example, certain types of medical imaging orders (and data associated with the orders) may be subject to a rule that indicates further prep is required, whereas time-sensitive medical imaging orders may be subject to a rule that precludes further prep. Other analyses by the prep rule engine (in evaluation 330) may involve an analysis of the type of order or study to determine whether information is missing or incorrect, whether images are not in a correct display state, or like evaluations on substantive study information.

If the evaluation by the prep rule engine (evaluation 330) indicates the usefulness of further coordination and preparation of the medical imaging procedure data, then the coordination and preparation of the medical imaging procedure data (operation 350) may be commenced after (or concurrent with) the initial assignment of the study to one or multiple evaluators (operation 340). The initial assignment of the study to multiple evaluators may be performed even though the study is not visible or accessible for evaluation (e.g., the study is hidden, locked, or restricted) via the worklist of the respective initial evaluators.

For example, the multiple evaluators that receive the initial assignment may not be aware that their respective computer systems have received an initial assignment for a study evaluation, although the respective computer systems begin to receive and process image data for the study. Pre-loading and pre-caching activities may download or retrieve the relevant medical imaging procedure data (including order and image data) in the background to multiple available or pre-selected evaluators while the study awaits additional coordination and preparation actions, or while initial coordination and preparation actions are being conducted for the study. The study may be made visible (or accessible, or unlocked) on the worklist of multiple evaluators (or a particular designated evaluator) immediately after the completion of the coordination and preparation activities (operation 360), or after the completion of determined conditions that release the study for evaluation to the evaluator(s). In some examples, at the completion of the coordination and preparation activities, data such as bookmark data, an image manifest, or other image display state information is communicated to and loaded on the computer system of the evaluator(s), such as a particular evaluator who accepts the assignment and begins the diagnostic evaluation.

If the evaluation of the prep rule engine (in evaluation 330) indicates no need for preparation and coordination of the medical imaging data, or no further coordination and preparation actions (in operation 350) remain to be conducted, then the evaluation of the imaging data may be commenced with the assignment of the study to the evaluator(s) (operation 360). This study assignment may be accompanied by operations that make the order and the study data visible on the worklist of the evaluator(s). As suggested above, the study may become visible on the worklist of the evaluator(s) during (but prior to) the conclusion of coordination and preparation actions (in operation 350). For example, if the data for the study is verified as complete, but only image orientation or presentation verification issues remain, then the study data may appear on the worklist of the evaluator(s), and a particular evaluator user may begin the diagnostic evaluation. The particular evaluator user may then receive updates to the bookmark data, image manifest, and image display states during the diagnostic evaluation as the coordination and preparation actions are completed by a preparing user.

Finally, the workflow concludes by the performance of the study evaluation by the particular evaluator user (operation 370), which results in the creation of a report or other data results. The report or data results then may be communicated to the original ordering medical facility (operation 380) or stored in a results medical information database. The changes to the study data, and the creation of metadata associated with the study data changes, that occur with the coordination and preparation actions may be leveraged by the evaluating user. For example, corrected or supplemented metadata information (including image measurements and diagnostic information) supplied by the coordination and preparation actions may be pre-populated in evaluator reports or report data. All or portions of the performance of the study evaluation (operation 370) may occur in real-time during or concurrent with the performance of the coordination and preparation actions (operation 350).

Figure 4:
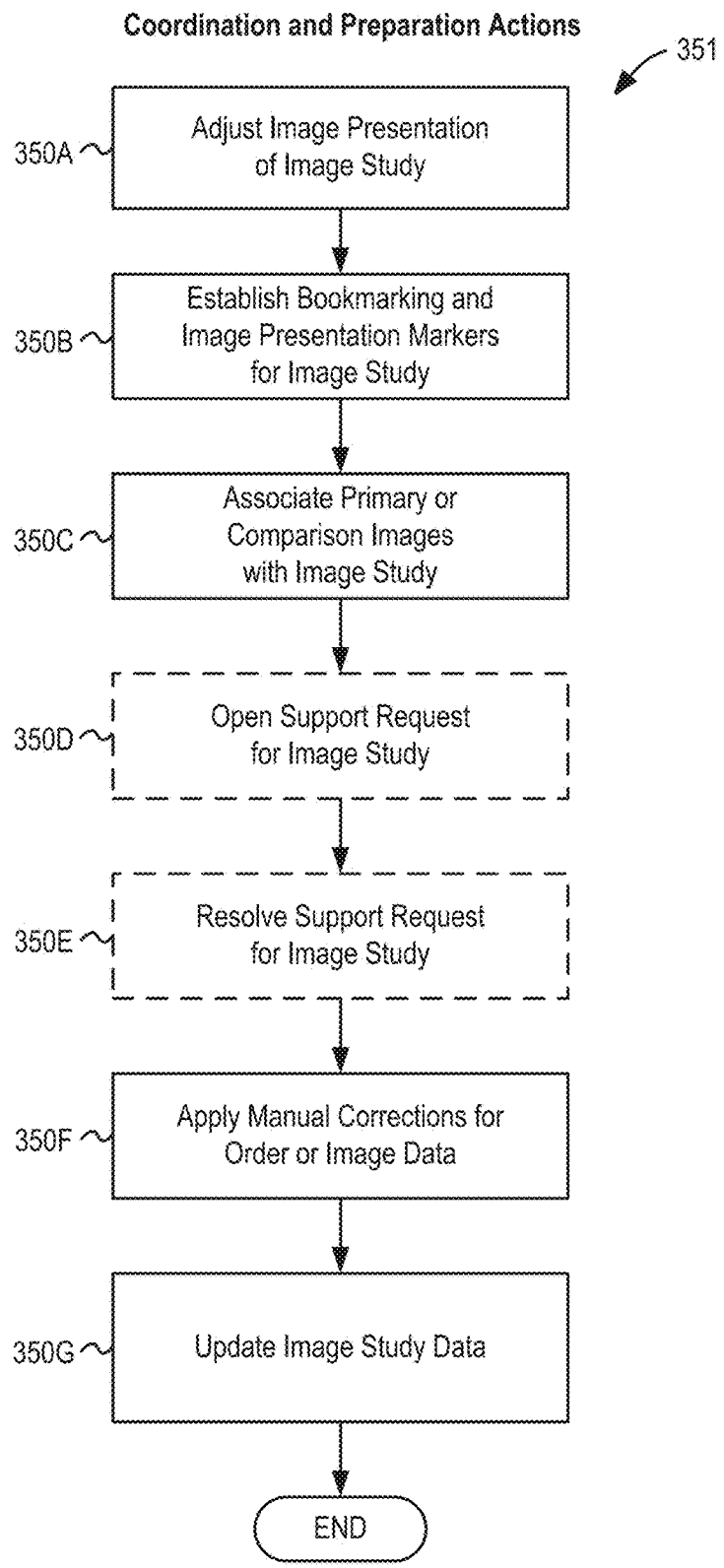
FIG. 4 illustrates a flowchart of a process for coordination and preparation of data for a medical imaging order according to an example described herein.

FIG. 4 illustrates a flowchart 351 of the various operations that may be performed by the coordination and preparation actions (operation 350) suggested in FIG. 3, such as operations conducted as part of an image review preparation protocol. Although the flowchart 351 depicts various operations in a sequence, it will be understood that the coordination and preparation actions (of operations 350A-350G) may be performed in an alternate sequence, or performed in response to the detection of certain conditions or events.

As shown in the flowchart 351, the coordination and processing operations may include: adjusting image presentation (operation 350A), which may involve changes to the orientation, window/level, contrast, visibility, hanging, or arrangement of visual images (and associated series and studies of the visual images); establishing bookmarking and image presentation markers (operation 350B), which may involve annotating visual image displays and tracking specific viewing or presentation states of visual image displays; and associating primary or comparison images with a study (operation 350C), which may involve retrieval, processing, and review of image data from a remote database, archive, or other image data store. If necessary data is missing from the study that prevents completion of one or more of these operations (or subsequent evaluation of the study), a support request may be opened (operation 350D) such as with a request to an operations center, medical facility, or monitoring location. The preparation status of the study may remain "open" or in a "pending" state until the resolution of the support request (operation 350E). In other scenarios, if the support request has been opened, the study will continue for evaluation by the evaluator, but relevant missing data fields of the study may be flagged or identified.

Based on the operations above and the results of any support request, additional manual corrections or changes may be applied to order data or image data (operation 350F). For example, manual changes from the original order data may be established to supplement incomplete data fields, supply missing medical information, or correct incorrectly identified scenarios (such as radiology images taken with contrast but labeled as without contrast). Based on the preceding updates and changes in the coordination and preparation actions, and any study data received from the preparing user, the data associated for the image study is updated or supplemented (operation 350G).

In connection with operations at the medical imaging data coordination and preparation system, a plurality of automated rules may be applied to implement the preceding actions as automated changes to the medical imaging procedure data. For example, items of information (such as misspelled data fields) can be automatically detected and corrected by a computer system. In some examples, automated rules may be processed prior to any preparation or coordination activities by human actors such as by the preparing user. In other examples, the changes from the medical imaging procedure data are human-assisted, such as would be provided in a graphical user interface allowing a preparing user to review and reject or accept changes to the items of information. Accordingly, the coordination and preparation actions may involve any number of manual adjustments for the presentation of the image study, consistent with the computer-aided, computer-assisted, or data-driven techniques described herein.

In connection with the evaluation of prior or comparison studies, the preparing user may be presented with a detailed patient timeline to review prior medical comparisons. For example, a timeline view may be compiled in a graphical user interface to display and hang prior imaging studies, imaging reports, and relevant medical evaluation information that would assist the image evaluation. This timeline view may be presented to the preparing user to receive markings and annotations by the preparing user. For example, the preparing user may be provided with the ability to select which study of a set of previous radiology studies to use as the prior study, or to select which particular study, series, or image of a study is the most relevant recent comparison for purposes of the specific medical evaluation being performed. This timeline functionality may be integrated with retrieve/query features of a PACS system, such as a PACS system of the originating medical facility or of a radiology medical practice. In further examples, automated techniques may be used to pre-select a most relevant comparison image based on scoring metrics and image analysis. However, such automated techniques may be used in combination with actions of the preparing user to present an interface to verify or confirm an automatic selection of this comparison image.

In further examples, graphical user interfaces (GUIs) may be designed to receive interactions and updates to the medical imaging procedure data, as part of the preparation and coordination process. For example, a graphical user interface displayed to the preparing user may include a worklist to display a status of numerous medical imaging orders. This worklist may include an indication of high-priority orders or orders requiring immediate attention by the preparing user. Further examples of worklists for preparing and evaluating multiple medical imaging studies are described below.

In some examples, some or all functions of the preparing user may be conducted by a radiology practitioner assistant (e.g., an individual who is a certified and registered radiographer), or other medically trained personnel. Further, a radiology practitioner assistant may perform initial medical evaluation actions (including establishing medical diagnoses, reports, and findings) during the coordination and processing actions, with such evaluation actions being later reviewed and confirmed by an evaluating radiologist. In other examples, the functions of the preparing user may be limited to basic data entry and image modification, such as may be performed by a radiology technician or similarly trained person.

Figure 5A:
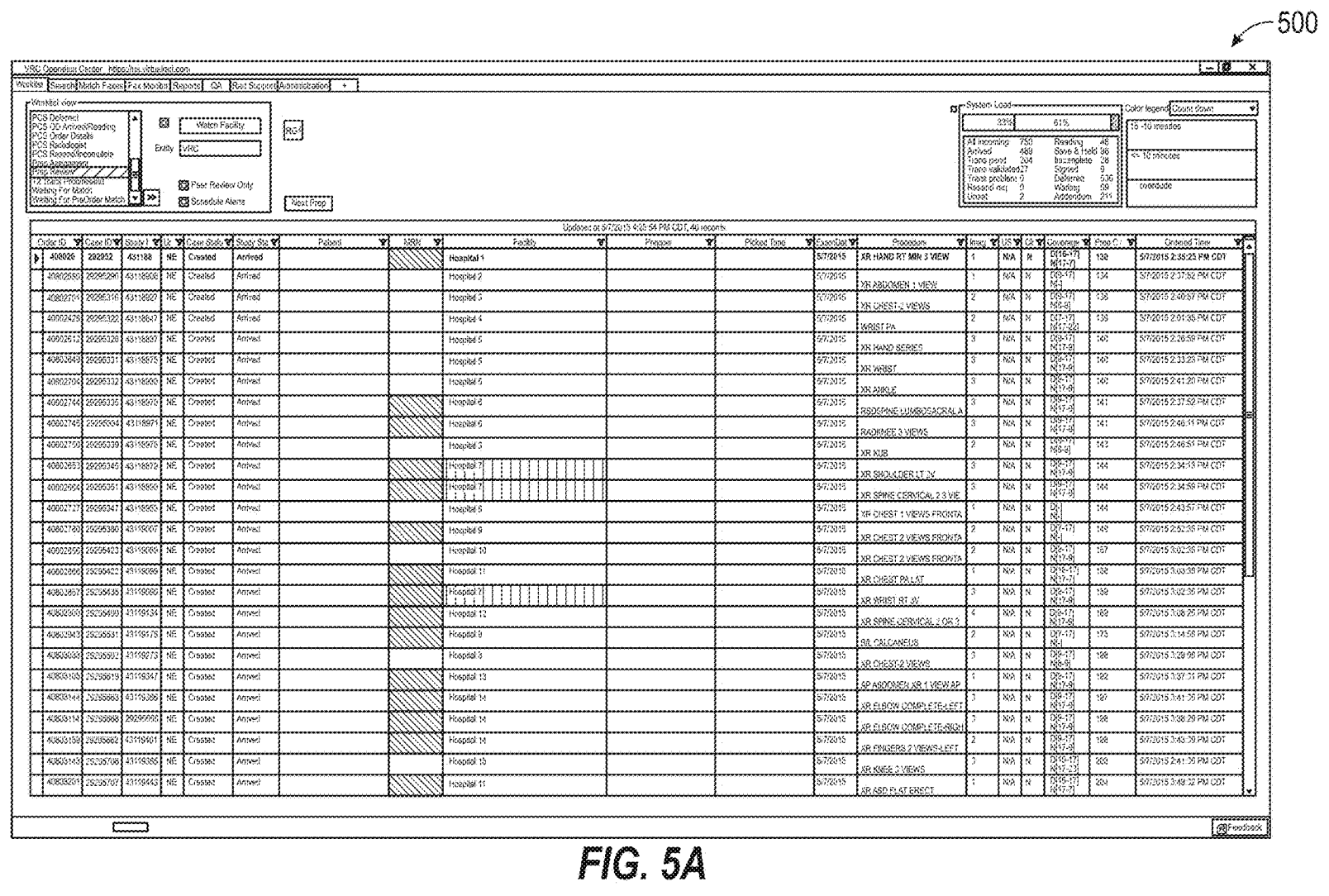

FIG. 5A illustrates a worklist graphical user interface 500, provided to a preparing user (e.g., preparer), such as would be provided at the data modification interface 254 operated in the coordination and preparation system 250 of FIG. 2. The worklist graphical user interface 500 may include various highlights, flags, or other indications of data fields that are determined to be incomplete. The preparing user may utilize the worklist graphical user interface 500 to access data for one or a plurality of studies, with the worklist capable of being filtered based on data fields such as status, facility, patient information, time, imaging source, and other pre-determined or calculated characteristics.

Figure 5B:
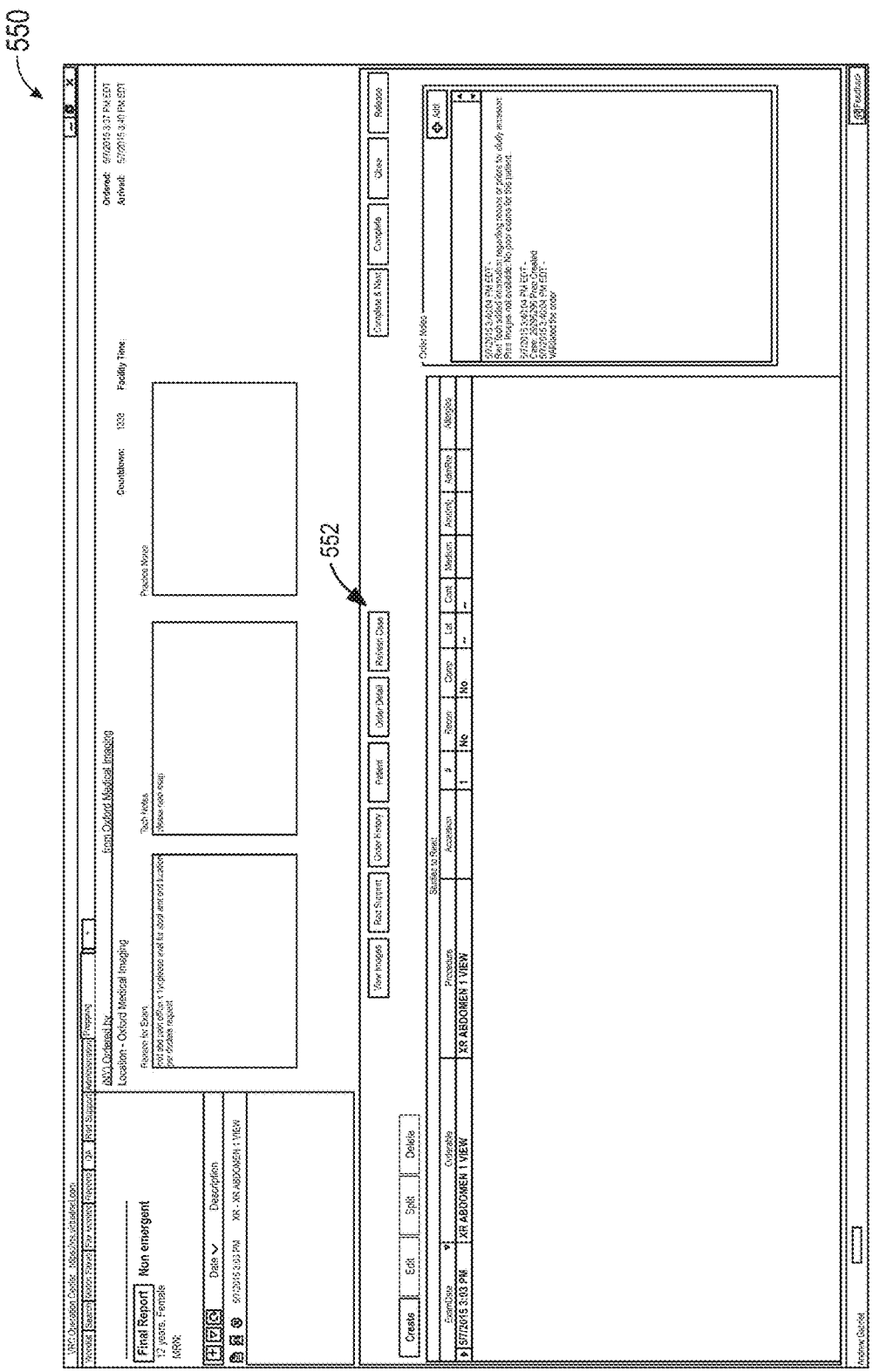
FIG. 5B illustrates a study preparation graphical user interface for management of a medical imaging study by an evaluating user according to an example described herein.

FIG. 5B illustrates a study preparation graphical user interface 550, provided to a preparing user (e.g., preparer), such as would be provided at the data modification interface 254 operated in the coordination and preparation system 250 of FIG. 2. This study preparation interface may be provided as a result of the selection of a particular study on a worklist for the preparing user, and may include information relative to a particular study. The study preparation interface or an equivalent user interface may offer the preparing user with a subset (or an extension of) the control to access and manipulate study and study data that are typically managed by administrative users, such as operations center users. For example, the study preparation graphical user interface 550 includes controls 552 to view images, access order support, view order information, view patient information, or refresh case details. Accordingly, the preparing user may be able to review or manage data individually or collectively for a variety of studies, including studies yet to be assigned for a plurality of evaluators.

Within the study graphical user interface 550, various options can be provided to the preparing user to change and modify study data and study data characteristics for a particular study. The study graphical user interface 550 may be arranged to provide access to other data sources (such as image archives) where the preparing user can obtain additional relevant information. A further option can be provided to indicate when the particular study is ready for review, to escalate the study to a support center, and the like.

FIG. 6A illustrates a worklist graphical user interface 600, provided to an evaluating user (e.g., radiologist) such as would be provided at the worklist 262 operated in the medical imaging evaluation system 260. In some examples, the study will not be displayed on the worklist graphical user interface 600 until preparation actions are complete and released by the preparing user with the graphical user interface 500. In other examples, the study may appear on the evaluator worklist graphical user interface 600 (even if preparation actions have started but are not complete) if a turnaround time elapses (such as a maximum amount of time). In still other examples, the study may appear on the worklist graphical user interface 600 if some but not all preparation actions are complete (such as after the preparing user has verified that the study meets some minimum requirements). For example, if the study has not been completely prepared yet, the data for the study may be updated and refreshed at the evaluation system 260.

Figure 6B:
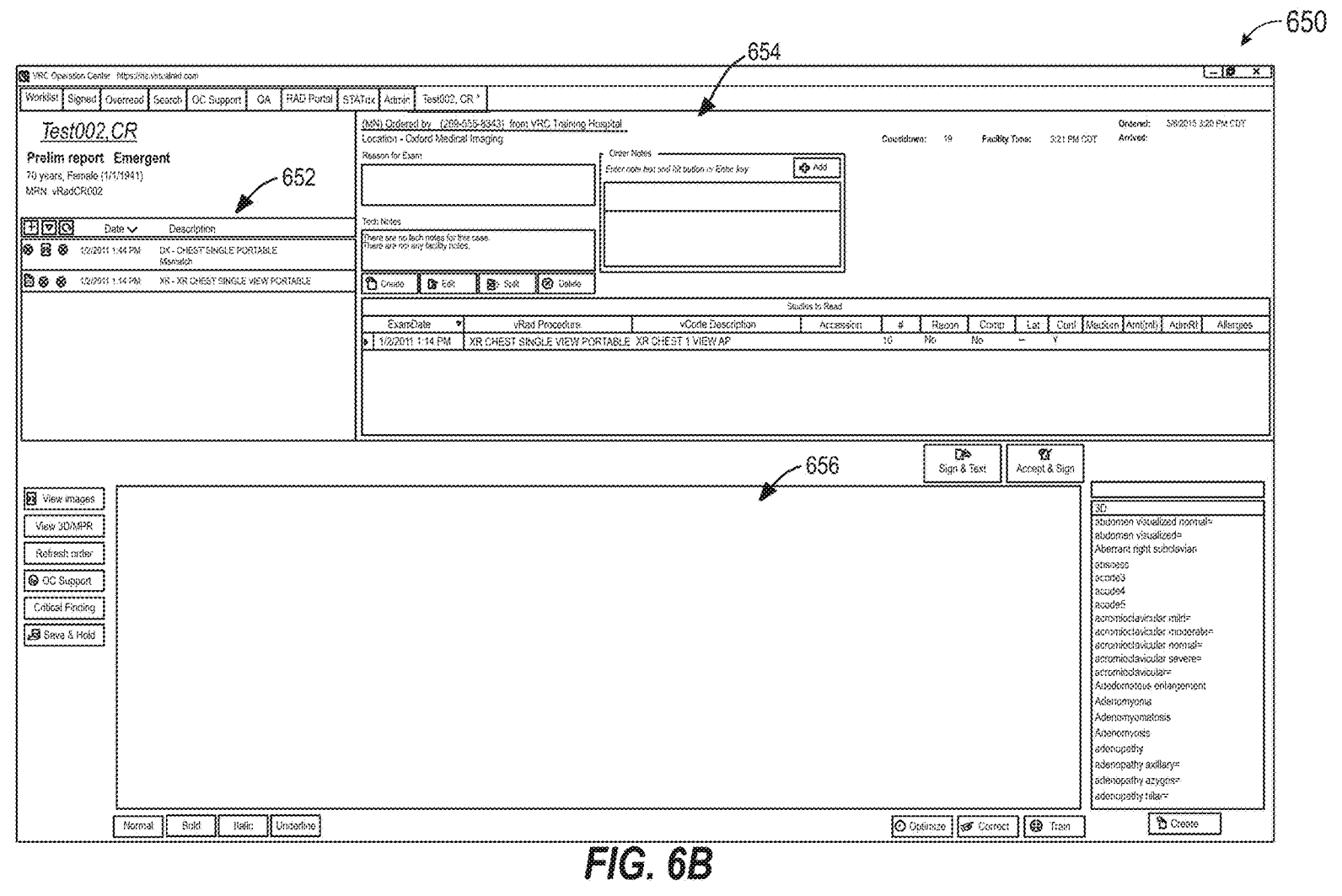

FIG. 6B illustrates a study reporting graphical user interface 650, provided to an evaluating user (e.g., radiologist) such as would be provided with reporting or study management functionality in the medical imaging evaluation system 260. Features of the study reporting graphical user interface 650 may include a timeline 652 (including data that may be supplemented or edited by the preparing user); study information 654 (including data that may be supplemented or edited by the preparing user); a study reporting result interface 656 (including data that may be supplemented or edited by the preparing user); and like interfaces which may be affected by the results of the preparing user. It will be understood that the data provided by the preparation actions described throughout this disclosure may be implemented in the study reporting graphical user interface 650 through various controls, inputs, and displays.

In accordance with the assignment process above, data for the medical imaging procedure may be sent to multiple evaluators. In this scenario, although multiple users have been preliminarily assigned the medical imaging study, the data of the study will not be accessible for evaluation until the study is released and the study appears on the worklist. Thus, data for the study (such as metadata, order data, or even the image data) may be cached to a plurality of possible evaluators (although the assignment may change), and the study will not be visible to the possible evaluators until certain conditions have completed. These conditions may include: when the study is completely prepped (or certain prepping actions have occurred); the turn-around-time expires; or if the worklist for the particular evaluator is empty. In these and other scenarios, the default action may involving perform the assignment to at least one best matched evaluator, regardless of the status of the coordination and preparation actions.

Based on the actions performed upon the data and the display by the particular evaluating user and the preparing user, the system may learn preferences and necessary changes to implement for subsequent imaging studies. Accordingly, changes that are repeated or errors that are repeatedly detected may be corrected or supplemented with automated rules. Other techniques may be used for logging and recording changes in presentation and style for particular preparing users and evaluating users. Logging also may be performed to determine which types of changes are commonly implemented by preparing users, versus evaluating users, including the creation of prompts or suggestions for preparing users if the change is commonly performed by evaluating users (or a particular evaluating user). In further examples, changes from respective evaluating users (e.g., radiologists) including visual display preferences can be logged, monitored, and adapted into rules and automated changes.

Figure 7:
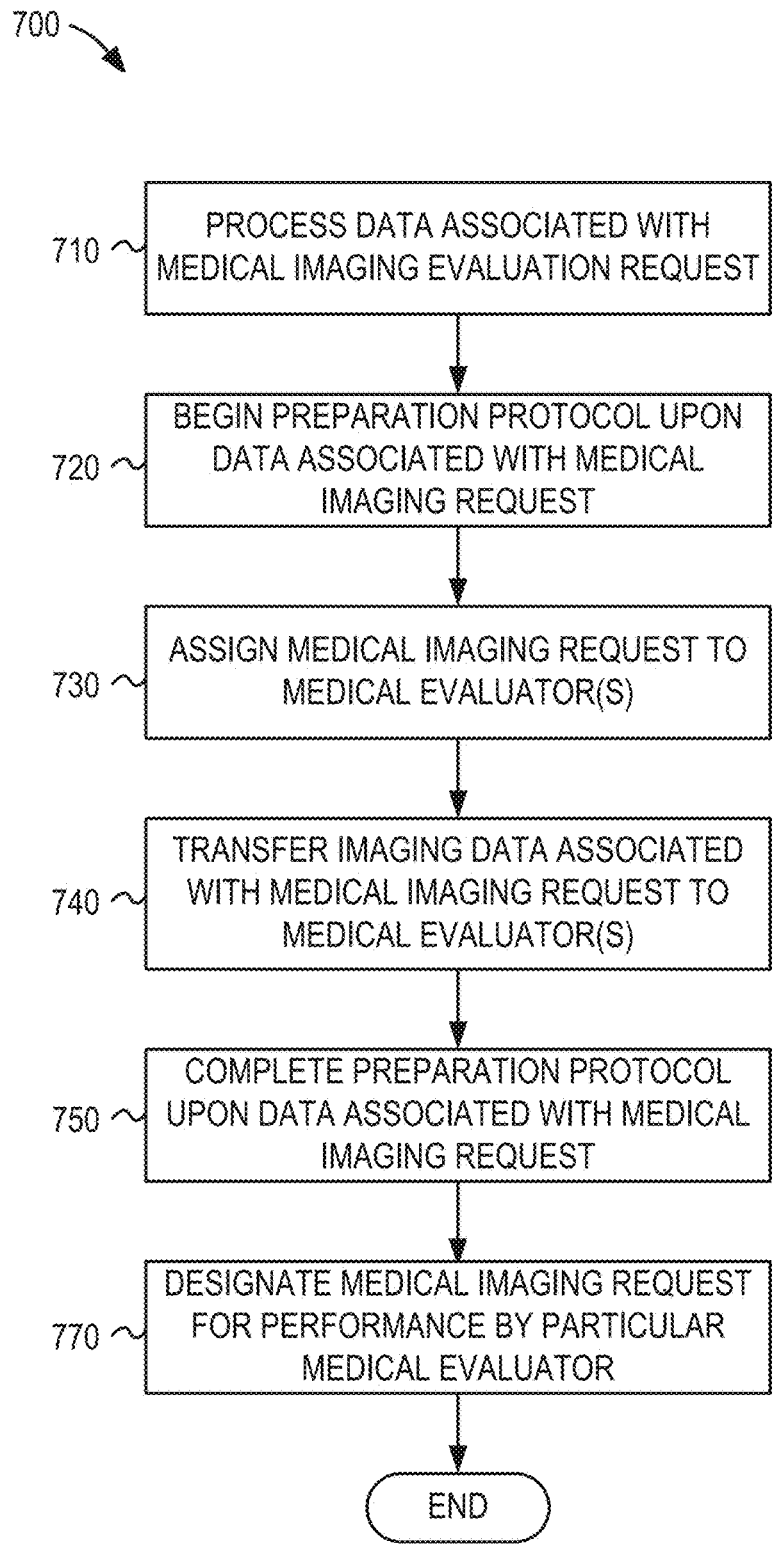
FIG. 7 illustrates a flowchart of example workflow operations performed for processing data produced from a particular medical imaging study according to an example described herein.

FIG. 7 illustrates a flowchart 700 of an example workflow for processing data produced from a particular medical imaging study according to an example described herein. The particular sequence depicted in the flowchart 700 is illustrated to emphasize the end-to-end actions which may occur in image processing and evaluation activities, such as for processing of radiology images and orders. However, it will be understood that the sequence of operations may vary depending on the precise data operations to be performed upon the study data produced by the imaging procedure and the originating medical facility, the conditions present when evaluating the study data, the state of the study data (including the number of errors in the study data), and human actions used to effect the preparation or coordination actions.

The flowchart 700 illustrates a series of operations executable with an image processing system, such as the system configuration 100 or specific components of the imaging order processing system 102. These operations include the processing of data associated with a request for a medical imaging evaluation data (e.g., processing of order data or image data originating from a medical imaging procedure) (operation 710). This data is processed to determine the particular characteristics and type of the imaging procedure, and whether preparation and coordination is required (or available).

Based on identified information from the procedure data, the characteristics of the procedure can be analyzed, and a preparation protocol may be executed upon the data (operation 720). For example, the preparation protocol may involve an evaluation of order data and image data metadata, to apply automated rules and corrections to study data. The preparation protocol may also involve the use of human-assisted review and corrections, consistent with the actions described in FIGS. 2, 3, and 4 above.

Based on the preparation protocol, the medical imaging request may be initially assigned to one or more medical evaluators. In some scenarios, order data, metadata, or image data for the medical imaging study may be transferred to (e.g., copied, downloaded, or pre-cached) a plurality of medical evaluators (operation 740), but not visible or accessible on the worklist of the evaluators, after the preparation protocol has begun. The preparation protocol continues and is ultimately completed upon the data (operation 750).

Upon completion of the preparation protocol, at least one particular medical evaluator from the plurality of medical evaluators may be designated to perform the evaluation of the medical imaging data (operation 760). For example, this designation may occur in response to making the study visible on the worklist of the medical evaluator(s) in response to the preparation protocol being completed, in response to receiving an indication of certain actions in the preparation protocol being completed, or like conditions. In other examples, the designation of a study to a particular medical evaluator(s) (operation 760) may be conducted upon the occurrence of other conditions, such as a turnaround time elapsing, a worklist of the medical evaluator being empty, or like scenarios. Once the particular medical evaluator selects or otherwise confirms the receipt and acceptance of the study, the evaluation of the medical imaging data commences.

Figure 8:
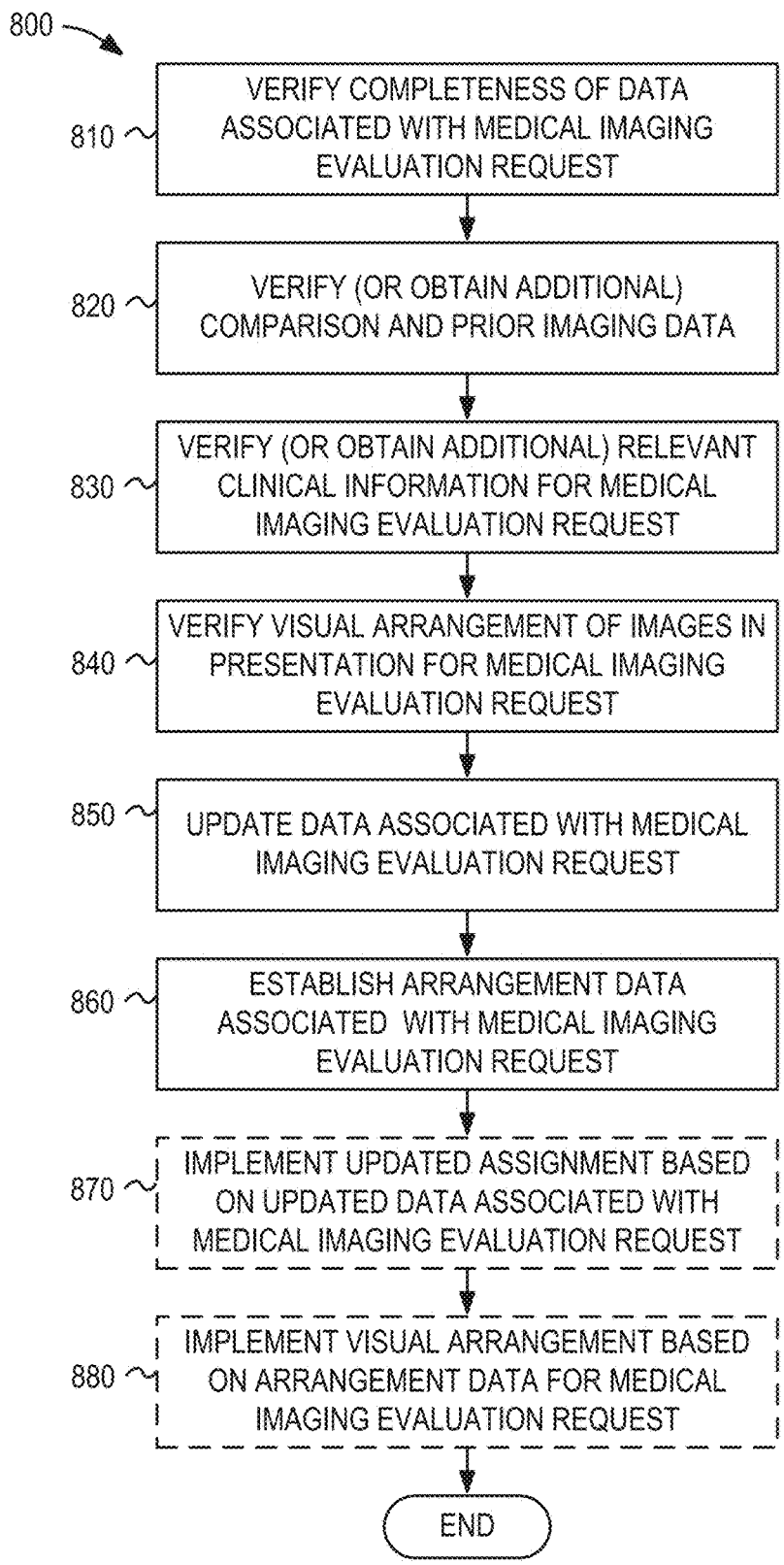
FIG. 8 illustrates a flowchart of additional workflow operations performed for processing data produced from a particular medical imaging study according to an example described herein.

FIG. 8 provides an illustration of a flowchart 800 of additional workflow operations that may be performed upon a particular imaging study (and associated imaging data) based on the preparation protocol described herein. The operations depicted in flowchart 800 are provided as example operations, but it will be understood that many of the depicted operations need not occur in sequence, but may occur in parallel, conditionally, or in other variations. Further, some or all of the operations depicted in flowchart 800 may occur in addition to the preparation protocol actions suggested in flowchart 700.

As illustrated, the various operations of flowchart 800 may include processing operations that are performed to accomplish preparation of the medical imaging procedure data for further evaluation. For example, the operations may include: verifying completeness of data (imaging data and request data) associated with a medical imaging evaluation request (e.g., a radiology order) (operation 810); verifying and obtaining comparison and prior imaging data (e.g., images from previous radiology studies for comparison) (operation 820); verifying and obtaining relevant clinical information in the evaluation request (e.g., medical information fields in a radiology order) (operation 830); and verifying a visual arrangement of images (operation 840).

Based on the result of the verifications, data associated with the medical imaging evaluation request may be updated (operation 850). Additionally, new data and metadata fields such as bookmarking, image manifests, or other arrangements of data for image presentation may be established (operation 860). Based on the new data and metadata fields, an updated assignment may be initiated to a particular evaluator (or set of evaluators) (operation 870). Further based on the new data and metadata fields, an updated visual arrangement of the study may be initiated at a graphical display of the particular evaluator (operation 880) who accepts or is otherwise designated to perform the evaluation.

Figure 9:
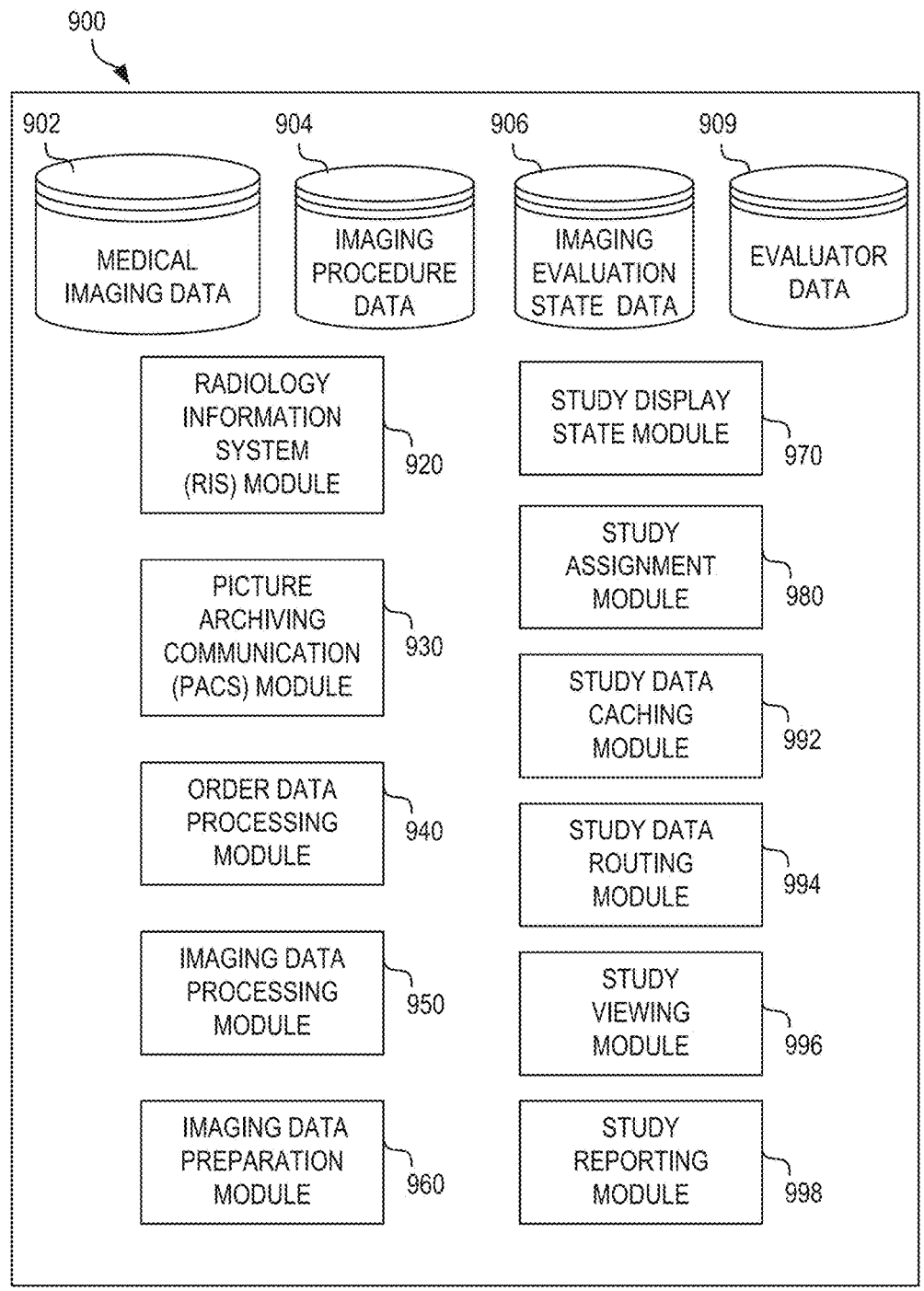
FIG. 9 illustrates a system configuration of a medical imaging data processing system arranged to process medical imaging data according to an example described herein.

FIG. 9 illustrates an example configuration of a system architecture 900 configured to implement the presently described processing system according to an example described herein. System architecture 900 may implement components such as the imaging order processing system 102 and features of the image review system 106 and the data pre-processing and coordination system 108. The system architecture 900 may include a radiology information system module 920, a picture archiving communication system module 930, an order data processing module 940, an image data processing module 950, an image data preparation module 960, a study display state module 970, a study assignment module 980, a study data caching module 992, a study data routing module 994, a study viewing module 996, and a study reporting module 998. In operation with these modules, the system architecture 900 may further include a plurality of databases or data stores, including a medical imaging database 902, an imaging procedure database 904, an imaging evaluation state database 906, and an evaluator database 908.

The medical imaging database 902 may provide a location for storage of imaging data (and metadata) for medical imaging procedures and associated studies. The imaging procedure database 904 may provide a location for storage of information to identify and process information for respective medical imaging procedures. The imaging evaluation state database 906 may provide a location for storage of metadata for imaging evaluation states including image manifests, bookmarks, annotations, and data fields used to perform respective image evaluations. The evaluator database 908 may provide a location for storage of information specific to evaluator preferences, capabilities, and characteristics related to the display of study images at an evaluator.

The various modules may perform functional operations to effect the processing, coordination, and assignment techniques described herein. For example, the radiology information system module 920 may be used to provide respective information processing functions of a RIS. The picture archiving communication system module 930 may be used to provide image storage and access features of a Picture Archiving Communication System (PACS). The order data processing module 940 may be used to process orders, and determine relevant information for pre-processing data of studies for evaluation. The image data processing module 950 may be used to request, receive, validate, and store images of studies for evaluation. The image data preparation module 960 may be used to perform imaging processing operations on imaging data obtained from a set of data associated with a medical imaging procedure, or from a customer imaging device, an image archive, medical facility data store, or other imaging data source.

The study display state module 970 may be used to provide consistent review of a study state between a preparing user and an evaluating user, or to establish and provide custom study viewing outputs (such as hanging protocols, display characteristics, and the like) based on the characteristics of the imaging study. The study assignment module 980 may be used to determine a preliminary assignment or listing of the study on a worklist for one or more medical evaluators, or to implement a finalized assignment of the study for evaluation by a particular evaluator who accepts or is otherwise confirmed to conduct the study. The study data caching module 992 may be used to coordinate pre-caching and pre-loading operations to computer workstations and network locations associated with one or more medical evaluators, in connection with study initial and finalized assignments and the associated imaging and study state data for the evaluation. The study data routing module 994 may be used to route, obtain, or direct imaging data and study state data for study evaluations among different medical platforms and locations based on the preparation actions, such as directing a radiology study to be read on-site versus remotely, or facilitating a request for imaging data to be obtained from a medical facility or image archive. The study viewing module 996 may be used to view studies (and specific types of rendering data) on screen by an evaluating user. The study reporting module 998 may be used to establish reporting functions for the evaluating user, either from a report that is primarily created by the evaluating user, or pre-populated by a previous reviewer such as a radiology practitioner assistant (RPA).

Figure 10:
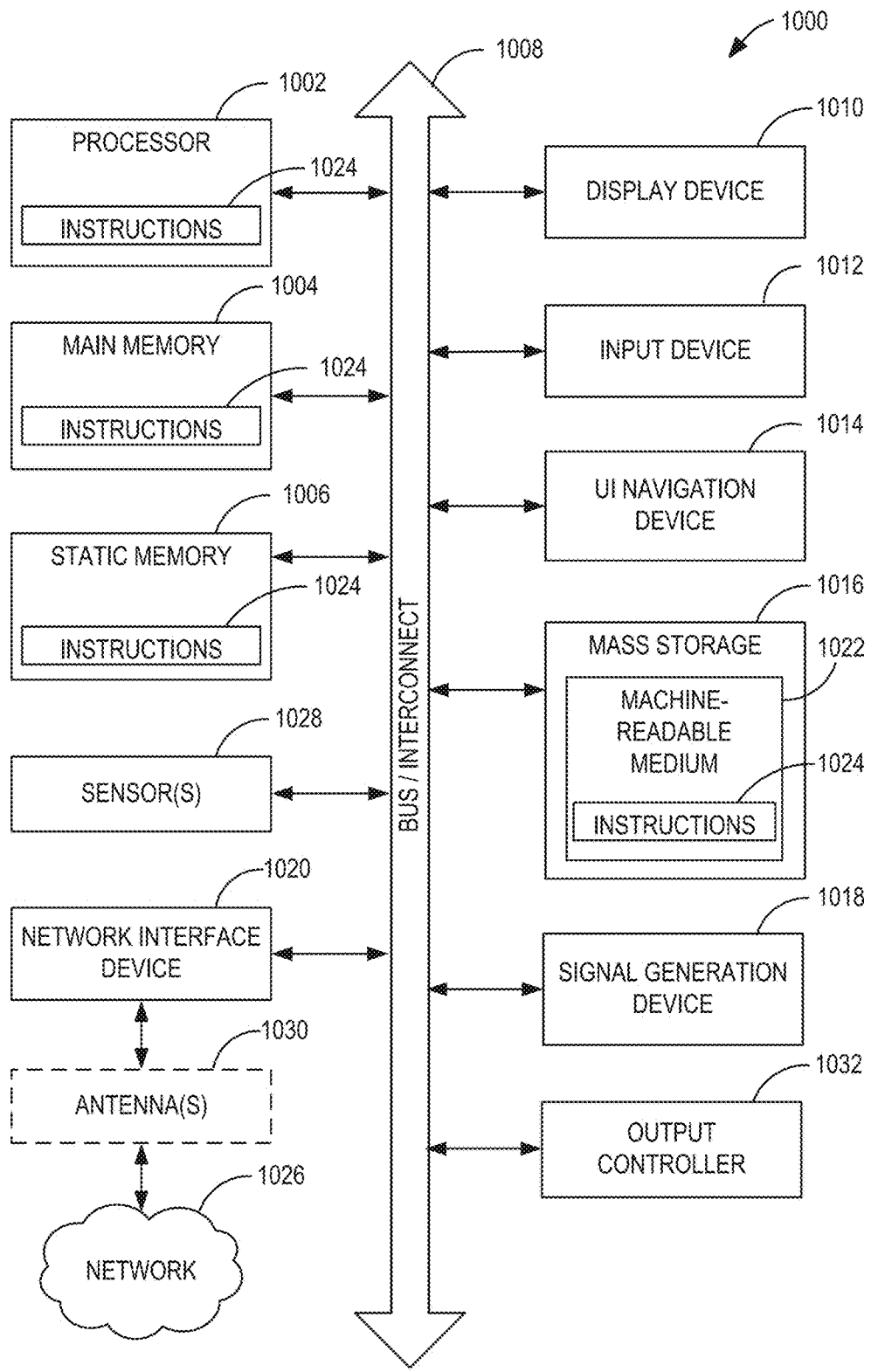
FIG. 10 illustrates an example of a machine configured to perform computing operations according to an example described herein.

FIG. 10 is a block diagram illustrating an example computing system machine 1000 upon which any one or more of the methodologies herein discussed may be run according to an example described herein. Computer system 1000 may be embodied as a computing device, providing operations of the components featured in the various figures, including components of the imaging order processing system 102, the imaging system 104, the image review system 106, the data pre-processing and coordination system 108, modules and data storage elements in system architecture 900, or any other processing or computing platform or component described or referred to herein. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The computer system machine may be a personal computer (PC) that may or may not be portable (e.g., a notebook or a netbook), a tablet, a Personal Digital Assistant (PDA), a mobile telephone or smartphone, a web appliance, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 1000 includes a processor 1002 (e.g., a central processing unit (CPU), a graphics processing unit (GPU) or both), a main memory 1004 and a static memory 1006, which communicate with each other via an interconnect 1008 (e.g., a link, a bus, etc.). The computer system 1000 may further include a video display unit 1010, an alphanumeric input device 1012 (e.g., a keyboard), and a user interface (UI) navigation device 1014 (e.g., a mouse). In one embodiment, the video display unit 1010, input device 1012 and UI navigation device 1014 are a touch screen display. The computer system 1000 may additionally include a storage device 1016 (e.g., a drive unit), a signal generation device 1018 (e.g., a speaker), an output controller 1032, and a network interface device 1020 (which may include or operably communicate with one or more antennas 1030, transceivers, or other wireless communications hardware), and one or more sensors 1028.

The storage device 1016 includes a machine-readable medium 1022 on which is stored one or more sets of data structures and instructions 1024 (e.g., software) embodying or utilized by any one or more of the methodologies or functions described herein. The instructions 1024 may also reside, completely or at least partially, within the main memory 1004, static memory 1006, and/or within the processor 1002 during execution thereof by the computer system 1000, with the main memory 1004, static memory 1006, and the processor 1002 constituting machine-readable media.

While the machine-readable medium 1022 is illustrated in an example embodiment to be a single medium, the term "machine-readable medium" may include a single medium or multiple media (e.g., a centralized or distributed database, and/or associated caches and servers) that store the one or more instructions 1024. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, optical media, and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1024 may further be transmitted or received over a communications network 1026 using a transmission medium via the network interface device 1020 utilizing any one of a number of well-known transfer protocols (e.g., HTTP). Examples of communication networks include a local area network (LAN), wide area network (WAN), the Internet, mobile telephone networks, Plain Old Telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Other applicable network configurations may be included within the scope of the presently described communication networks. Although examples were provided with reference to a local area wireless network configuration and a wide area Internet network connection, it will be understood that communications may also be facilitated using any number of personal area networks, LANs, and WANs, using any combination of wired or wireless transmission mediums.

The embodiments described above may be implemented in one or a combination of hardware, firmware, and software. For example, the modules in the system architecture 900 of the processing system may be client-operated software or be embodied on a server running an operating system with software running thereon. While some embodiments described herein illustrate only a single machine or device, the terms "system", "machine", or "device" shall also be taken to include any collection of machines or devices that individually or jointly execute a set (or multiple sets) of instructions to perform any one or more of the methodologies discussed herein.

Examples, as described herein, may include, or may operate on, logic or a number of components, modules, or mechanisms. Modules are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine readable medium. In an example, the software, when executed by the underlying hardware of the module, causes the hardware to perform the specified operations.

Accordingly, the term "module" is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

Additional examples of the presently described method, system, and device embodiments are suggested according to the structures and techniques described herein. Other non-limiting examples may be configured to operate separately, or can be combined in any permutation or combination with any one or more of the other examples provided above or throughout the present disclosure.

Example 1 includes subject matter (such as a method, means for performing acts, machine readable medium including instructions that when performed by a machine cause the machine to performs acts, or an apparatus to perform) comprising: electronically processing data associated with a medical imaging study, the data associated with the medical imaging study including imaging data from a medical imaging procedure; performing a preparation protocol upon the data associated with the medical imaging study, the preparation protocol establishing preparation data to affect an evaluation of the medical imaging study; performing an electronic assignment of the medical imaging study to a medical evaluator, the electronic assignment being performed based on the data associated with the medical imaging study and the preparation data; and making the medical imaging study available to the medical evaluator for evaluation, the medical imaging study being made available for evaluation in response to a completion of the performing of the preparation protocol; wherein the preparation data is used to affect a display of the imaging data to the medical evaluator within the evaluation of the medical imaging study.

In Example 2, the subject matter of Example 1 may include, wherein electronically processing the data associated with the medical imaging study includes determining whether a condition affects the evaluation of the medical imaging study, wherein the performing of the preparation protocol is initiated in response to determining that the condition affects the evaluation of the medical imaging study, and wherein the condition that affects the evaluation of the medical imaging study includes at least one of: missing information in the data associated with the medical imaging study, an error in the data associated with the medical imaging study, an incorrect display orientation of images in the imaging data, or an incorrect display arrangement of images in the imaging data.

In Example 3, the subject matter of any one of Examples 1 to 2 may include, the operations of the method transferring the imaging data associated with the medical imaging study to a computing device associated with the medical evaluator in response to the electronic assignment of the medical imaging study to the medical evaluator; wherein making the medical imaging study available to the medical evaluator for evaluation includes listing the medical imaging study on a worklist in a graphical user interface available to the medical evaluator; and wherein at least a portion of the data associated with the medical imaging study is pre-cached at the computing device associated with the medical evaluator prior to listing the medical imaging study on the worklist in the graphical user interface available to the medical evaluator.

In Example 4, the subject matter of any one of Examples 1 to 3 may include, wherein performing the preparation protocol upon the data associated with the medical imaging study includes creating the preparation data that modifies one or more data values of order data associated with the medical imaging study.

In Example 5, the subject matter of any one of Examples 1 to 4 may include, wherein performing the preparation protocol upon the data associated with the medical imaging study includes creating the preparation data that modifies one or more presentation characteristics of the imaging data associated with the medical imaging study.

In Example 6, the subject matter of any one of Examples 1 to 5 may include, wherein performing the preparation protocol upon the data associated with the medical imaging study includes creating data for a support request associated with the medical imaging study, the support request indicating additional information required for performance of the evaluation of the medical imaging study.

In Example 7, the subject matter of any one of Examples 1 to 6 may include, wherein performing the preparation protocol upon the data associated with the medical imaging study includes: identifying one or more comparison images for inclusion in the evaluation of the medical imaging study, the one or more comparison images used as a comparison with images in the imaging data from the medical imaging procedure; obtaining the one or more comparison images for inclusion in the evaluation of the medical imaging study; and associating data for the one or more comparison images with the medical imaging study.

In Example 8, the subject matter of any one of Examples 1 to 7 may include, the operations of the method performing an initial electronic assignment of the medical imaging study to the medical evaluator and one or more other medical evaluators, the electronic assignment being performed based on the data associated with the medical imaging study; and establishing an initial listing of the medical imaging study on a worklist available to the medical evaluator and respective worklists available to one or more other medical evaluators, the initial listing being established based on the data associated with the medical imaging study; and removing the initial listing of the medical imaging study on the worklist available to the one or more other medical evaluators in response to a designation of the study for evaluation to the medical evaluator.

In Example 9, the subject matter of any one of Examples 1 to 8 may include, wherein the designation of the study to the medical evaluator occurs in response to a selection of the medical imaging study in a graphical user interface via the worklist available to the medical evaluator.

In Example 10, the subject matter of any one of Examples 1 to 9 may include, the operations of the method making the medical imaging study available to the medical evaluator for evaluation, prior to a completion of the performing of the preparation protocol upon the data associated with the medical imaging study, based on one or more of: a worklist available to the medical evaluator being empty; a turn-around-time for evaluation of the medical imaging study exceeding a predetermined amount of time; or a priority indication for the medical imaging study.

In Example 11, the subject matter of any one of Examples 1 to 10 may include, wherein the medical imaging procedure is a radiological imaging procedure, wherein the imaging data from the medical imaging procedure includes radiology images produced for a radiology study, and wherein the medical imaging study is provided for a radiological read request for diagnostic evaluation of the radiology images produced for the radiology study.

Example 12 includes subject matter (such as embodied on a computer readable medium) comprising instructions for a computing machine configured to: process data associated with a medical imaging study, the data associated with the medical imaging study including imaging data from a medical imaging procedure; perform a preparation protocol upon the data associated with the medical imaging study, the preparation protocol establishing preparation data to affect an evaluation of the medical imaging study; assign the medical imaging study to a medical evaluator, based on the data associated with the medical imaging study and the preparation data; and modifying an availability of the medical imaging study for evaluation by the medical evaluator, the medical imaging study being made available for the evaluation by the medical evaluator in response to a completion of the preparation protocol; wherein the preparation data is used to affect a display of the imaging data to the medical evaluator within the evaluation of the medical imaging study.

In Example 13, the subject matter of Example 12 may include, the instructions further operable to cause the computing machine to perform operations that: detect a data condition in the data associated with the medical imaging study, the data condition including at least one of: missing information in the data associated with the medical imaging study, an error in the data associated with the medical imaging study, an incorrect orientation of images in the imaging data, or an incorrect arrangement of images in the imaging data; and process data for the medical imaging study to correct the data condition.

In Example 14, the subject matter of any one of Examples 12 to 13 may include, the instructions further operable to cause the computing machine to perform operations that: transfer the imaging data associated with the medical imaging study to a computing machine associated with the medical evaluator in response to assignment of the medical imaging study to the medical evaluator, wherein at least a portion of the data associated with the medical imaging study is cached at the computing machine associated with the medical evaluator prior to the medical imaging study being designated for performance by the medical evaluator.

In Example 15, the subject matter of any one of Examples 12 to 14 may include, wherein performing the preparation protocol upon the data associated with the medical imaging study is implemented by one or more operations that: create preparation data that modifies one or more data values of order data associated with the medical imaging study; create preparation data that modifies one or more presentation characteristics of the imaging data associated with the medical imaging study; create data for a support request associated with the medical imaging study; or associate data for at least one comparison image with the medical imaging study.

In Example 16, the subject matter of any one of Examples 12 to 15 may include, the instructions further operable to cause the computing machine to perform operations that:

establish an initial assignment of the medical imaging study to a plurality of other medical evaluators based on the data in the medical imaging study; designate the medical evaluator to perform evaluation of image data associated with the medical imaging study, wherein operations that designate the medical evaluator to perform evaluation of the image data are performed subsequent to the completion of the preparation protocol upon the data in the medical imaging study.

In Example 17, the subject matter of any one of Examples 12 to 16 may include, wherein the medical imaging study is made available to the medical evaluator for evaluation, prior to a completion of the preparation protocol upon the data associated with the medical imaging study, based on one or more of: a worklist operated by the medical evaluator reaching a predetermined condition; a turn-around-time for evaluation of the medical imaging study exceeding a predetermined amount of time; or a priority indication for the medical imaging study.

Example 18 includes subject matter (such as a device, apparatus, or machine) comprising: at least one hardware processor and memory; a preparation module implemented with the at least one hardware processor and memory, the preparation module configured to: process data associated with a medical imaging study, the data associated with the medical imaging study including imaging data from a medical imaging procedure, and perform a preparation protocol upon the data associated with the medical imaging study, the preparation protocol establishing preparation data to affect an evaluation of the medical imaging study; a study assignment module implemented with the at least one hardware processor and memory, the study assignment module configured to: assign the medical imaging study to a medical evaluator, based on the data associated with the medical imaging study and the preparation data; and a study display state module implemented with the at least one hardware processor and memory, the study display state module configured to: affect a display of the imaging data at a computing device of the medical evaluator for the evaluation of the medical imaging study, based on an updated study display state indicated by the preparation data.

In Example 19, the subject matter of Example 18 may include, a study data caching module implemented with the at least one hardware processor and memory, the study data caching module configured to: transfer the imaging data associated with the medical imaging study to a computing machine associated with the medical evaluator in response to assignment of the medical imaging study to the medical evaluator, wherein at least a portion of the data associated with the medical imaging study is cached at the computing machine associated with the medical evaluator prior to a designation of the study for evaluation to the medical evaluator.

In Example 20, the subject matter of any one of Examples 18 to 19 may include, wherein the medical imaging procedure produces data for a radiology study, the system a radiology information system (RIS) module, the RIS module configured to correlate the radiology study in a RIS instance with the medical imaging procedure, and provide order data produced for the medical imaging procedure.

In Example 21, the subject matter of any one of Examples 18 to 20 may include, wherein the medical imaging procedure produces data for a radiology study, and the system a Picture Archiving Communication System (PACS) module, the PACS module configured to provide the imaging data produced from the medical imaging procedure.

In Example 22, the subject matter of any one of Examples 18 to 21 may include, the system an image data processing module configured to obtain information from image data associated with the medical imaging procedure; and an order data processing module configured to obtain information from order data associated with the medical imaging procedure; wherein the preparation module is further configured to detect a data condition in information from the image data or the order data, the data condition including at least one of: missing information in the image data or the order data, an error in the image data or the order data, an incorrect orientation of images in the image data, or an incorrect arrangement of images in the image data.

In Example 23, the subject matter of any one of Examples 18 to 22 may include, a study viewing module implemented with the at least one hardware processor and memory, the study viewing module configured to display the study to the medical evaluator based on state changes to the study, wherein the study display state module is configured to process data for the medical imaging study to correct the data condition in a display of the updated study display state to the medical evaluator.

In Example 24, the subject matter of any one of Examples 18 to 23 may include, a study reporting module implemented with the at least one hardware processor and memory, the study reporting module configured to display a report for the study for editing by the medical evaluator, based on state changes to the study.

What is claimed is:

1. A method for management of a medical imaging workflow, the method implemented by a computing device through an execution of operations on at least one processor and memory of the computing device, with the operations comprising:
   electronically processing data associated with a medical imaging study, the data associated with the medical imaging study including imaging data from a medical imaging procedure;
   performing a preparation protocol upon the data associated with the medical imaging study, the preparation protocol establishing preparation data to affect an evaluation of the medical imaging study;
   performing an electronic assignment of the medical imaging study to a medical evaluator, the electronic assignment being performed based on the data associated with the medical imaging study and the preparation data; and
   making the medical imaging study available to the medical evaluator for evaluation, the medical imaging study being made available for evaluation in response to a completion of the performing of the preparation protocol;
   wherein the preparation data is used to affect a display of the imaging data to the medical evaluator within the evaluation of the medical imaging study.

2. The method of claim 1, wherein electronically processing the data associated with the medical imaging study includes determining whether a condition affects the evaluation of the medical imaging study, wherein the performing of the preparation protocol is initiated in response to determining that the condition affects the evaluation of the medical imaging study, and
   wherein the condition that affects the evaluation of the medical imaging study includes at least one of: missing information in the data associated with the medical imaging study, an error in the data associated with the medical imaging study, an incorrect display orientation of images in the imaging data, or an incorrect display arrangement of images in the imaging data.

3. The method of claim 1, the operations of the method comprising:
transferring the imaging data associated with the medical imaging study to a computing device associated with the medical evaluator in response to the electronic assignment of the medical imaging study to the medical evaluator;
wherein making the medical imaging study available to the medical evaluator for evaluation includes listing the medical imaging study on a worklist in a graphical user interface available to the medical evaluator; and
wherein at least a portion of the data associated with the medical imaging study is pre-cached at the computing device associated with the medical evaluator prior to listing the medical imaging study on the worklist in the graphical user interface available to the medical evaluator.

4. The method of claim 1, wherein performing the preparation protocol upon the data associated with the medical imaging study includes creating the preparation data that modifies one or more data values of order data associated with the medical imaging study.

5. The method of claim 1, wherein performing the preparation protocol upon the data associated with the medical imaging study includes creating the preparation data that modifies one or more presentation characteristics of the imaging data associated with the medical imaging study.

6. The method of claim 1, wherein performing the preparation protocol upon the data associated with the medical imaging study includes creating data for a support request associated with the medical imaging study, the support request indicating additional information required for performance of the evaluation of the medical imaging study.

7. The method of claim 1, wherein performing the preparation protocol upon the data associated with the medical imaging study includes:
identifying one or more comparison images for inclusion in the evaluation of the medical imaging study, the one or more comparison images used as a comparison with images in the imaging data from the medical imaging procedure;
obtaining the one or more comparison images for inclusion in the evaluation of the medical imaging study; and
associating data for the one or more comparison images with the medical imaging study.

8. The method of claim 1, the operations of the method comprising:
performing an initial electronic assignment of the medical imaging study to the medical evaluator and one or more other medical evaluators, the electronic assignment being performed based on the data associated with the medical imaging study; and
establishing an initial listing of the medical imaging study on a worklist available to the medical evaluator and respective worklists available to one or more other medical evaluators, the initial listing being established based on the data associated with the medical imaging study; and
removing the initial listing of the medical imaging study on the worklist available to the one or more other medical evaluators in response to a designation of the study for evaluation to the medical evaluator.

9. The method of claim 8, wherein the designation of the study to the medical evaluator occurs in response to a selection of the medical imaging study in a graphical user interface via the worklist available to the medical evaluator.

10. The method of claim 1, the operations of the method comprising:
making the medical imaging study available to the medical evaluator for evaluation, prior to a completion of the performing of the preparation protocol upon the data associated with the medical imaging study, based on one or more of:
a worklist available to the medical evaluator being empty;
a turn-around-time for evaluation of the medical imaging study exceeding a predetermined amount of time; or
a priority indication for the medical imaging study.

11. The method of claim 1, wherein the medical imaging procedure is a radiological imaging procedure, wherein the imaging data from the medical imaging procedure includes radiology images produced for a radiology study, and wherein the medical imaging study is provided for a radiological read request for diagnostic evaluation of the radiology images produced for the radiology study.

12. A non-transitory machine-readable medium, the machine-readable medium including instructions, which when executed by a computing machine having at least one hardware processor, cause the computing machine to perform operations that:
process data associated with a medical imaging study, the data associated with the medical imaging study including imaging data from a medical imaging procedure;
perform a preparation protocol upon the data associated with the medical imaging study, the preparation protocol establishing preparation data to affect an evaluation of the medical imaging study;
assign the medical imaging study to a medical evaluator, based on the data associated with the medical imaging study and the preparation data; and
modifying an availability of the medical imaging study for evaluation by the medical evaluator, the medical imaging study being made available for the evaluation by the medical evaluator in response to a completion of the preparation protocol;
wherein the preparation data is used to affect a display of the imaging data to the medical evaluator within the evaluation of the medical imaging study.

13. The machine-readable medium of claim 12, the instructions further operable to cause the computing machine to perform operations that:
detect a data condition in the data associated with the medical imaging study, the data condition including at least one of: missing information in the data associated with the medical imaging study, an error in the data associated with the medical imaging study, an incorrect orientation of images in the imaging data, or an incorrect arrangement of images in the imaging data; and
process data for the medical imaging study to correct the data condition.

14. The machine-readable medium of claim 12, the instructions further operable to cause the computing machine to perform operations that:
transfer the imaging data associated with the medical imaging study to a computing machine associated with the medical evaluator in response to assignment of the medical imaging study to the medical evaluator, wherein at least a portion of the data associated with the medical imaging study is cached at the computing machine associated with the medical evaluator prior to the medical imaging study being designated for performance by the medical evaluator.

15. The machine-readable medium of claim 12, wherein performing the preparation protocol upon the data associated with the medical imaging study is implemented by one or more operations that:
   create preparation data that modifies one or more data values of order data associated with the medical imaging study;
   create preparation data that modifies one or more presentation characteristics of the imaging data associated with the medical imaging study;
   create data for a support request associated with the medical imaging study; or
   associate data for at least one comparison image with the medical imaging study.

16. The machine-readable medium of claim 12, the instructions further operable to cause the computing machine to perform operations that:
   establish an initial assignment of the medical imaging study to a plurality of other medical evaluators based on the data in the medical imaging study;
   designate the medical evaluator to perform evaluation of image data associated with the medical imaging study, wherein operations that designate the medical evaluator to perform evaluation of the image data are performed subsequent to the completion of the preparation protocol upon the data in the medical imaging study.

17. The machine-readable medium of claim 12, wherein the medical imaging study is made available to the medical evaluator for evaluation, prior to a completion of the preparation protocol upon the data associated with the medical imaging study, based on one or more of:
   a worklist operated by the medical evaluator reaching a predetermined condition;
   a turn-around-time for evaluation of the medical imaging study exceeding a predetermined amount of time; or
   a priority indication for the medical imaging study.

18. A computer system, comprising:
   at least one hardware processor and memory;
   a preparation module implemented with the at least one hardware processor and memory, the preparation module configured to:
   process data associated with a medical imaging study, the data associated with the medical imaging study including imaging data from a medical imaging procedure, and
   perform a preparation protocol upon the data associated with the medical imaging study, the preparation protocol establishing preparation data to affect an evaluation of the medical imaging study;
   a study assignment module implemented with the at least one hardware processor and memory, the study assignment module configured to:
   assign the medical imaging study to a medical evaluator, based on the data associated with the medical imaging study and the preparation data; and
   a study display state module implemented with the at least one hardware processor and memory, the study display state module configured to:
   affect a display of the imaging data at a computing device of the medical evaluator for the evaluation of the medical imaging study, based on an updated study display state indicated by the preparation data.

19. The computer system of claim 18, the system further comprising:
   a study data caching module implemented with the at least one hardware processor and memory, the study data caching module configured to:
   transfer the imaging data associated with the medical imaging study to a computing machine associated with the medical evaluator in response to assignment of the medical imaging study to the medical evaluator, wherein at least a portion of the data associated with the medical imaging study is cached at the computing machine associated with the medical evaluator prior to a designation of the study for evaluation to the medical evaluator.

20. The computer system of claim 18, wherein the medical imaging procedure produces data for a radiology study, the system further comprising a radiology information system (RIS) module, the RIS module configured to correlate the radiology study in a RIS instance with the medical imaging procedure, and provide order data produced for the medical imaging procedure.

21. The computer system of claim 18, wherein the medical imaging procedure produces data for a radiology study, and the system further comprising a Picture Archiving Communication System (PACS) module, the PACS module configured to provide the imaging data produced from the medical imaging procedure.

22. The computer system of claim 18, the system further comprising:
   an image data processing module configured to obtain information from image data associated with the medical imaging procedure; and
   an order data processing module configured to obtain information from order data associated with the medical imaging procedure;
   wherein the preparation module is further configured to detect a data condition in information from the image data or the order data, the data condition including at least one of: missing information in the image data or the order data, an error in the image data or the order data, an incorrect orientation of images in the image data, or an incorrect arrangement of images in the image data.

23. The computer system of claim 22, the system further comprising:
   a study viewing module implemented with the at least one hardware processor and memory, the study viewing module configured to display the study to the medical evaluator based on state changes to the study, wherein the study display state module is configured to process data for the medical imaging study to correct the data condition in a display of the updated study display state to the medical evaluator.

24. The computer system of claim 22, the system further comprising:
   a study reporting module implemented with the at least one hardware processor and memory, the study reporting module configured to display a report for the study for editing by the medical evaluator, based on state changes to the study.

* * * * *